United States Patent [19]
French

[11] Patent Number: 5,437,024
[45] Date of Patent: Jul. 25, 1995

[54] SELECTIVE COMPUTER-GENERATED INFORMATION DISTRIBUTION SYSTEM BY COMPUTER PERIPHERAL EMULATION AND USE

[76] Inventor: Donald H. French, 200 Old Tree Trace, Roswell, Ga. 30075

[21] Appl. No.: 910,828

[22] Filed: Jul. 6, 1992

[51] Int. Cl.⁶ ............................................. G06F 17/00
[52] U.S. Cl. ............................... 395/600; 364/DIG. 1
[58] Field of Search .................................. 395/200, 600

[56] References Cited

U.S. PATENT DOCUMENTS

| | | | |
|---|---|---|---|
| 3,839,708 | 10/1974 | Bredesen et al. | 340/172.5 |
| 4,713,780 | 12/1987 | Schultz et al. | 364/514 |
| 4,835,372 | 5/1989 | Gombrich et al. | 235/375 |
| 4,893,270 | 1/1990 | Beck et al. | 364/900 |
| 4,933,846 | 6/1990 | Humphrey et al. | 364/200 |
| 4,974,254 | 11/1991 | Perine et al. | 379/100 |
| 5,040,132 | 8/1991 | Schuricht et al. | 364/523 |
| 5,265,205 | 11/1993 | Schröder | 395/200 |
| 5,274,547 | 12/1993 | Zoffel et al. | 364/408 |

OTHER PUBLICATIONS

Author: Datix Corporation, Norcross, Ga. Title: "Practi-Com, Linking Physicians with Hospitals"; Date: Unknown.

Primary Examiner—Thomas G. Black
Assistant Examiner—Peter Y. Wang
Attorney, Agent, or Firm—Jones & Askew

[57] ABSTRACT

An information distribution system operative for receiving a report in the form of a printer protocol-formatted digital data stream from a report source, identifying the report as being of particular classes and/or subclasses, identifying at least one intended recipient of the report from data contained in the report, and automatically distributing the report to at least one identified intended report recipient. The system includes a microcomputer-based controller having an input/output interface that emulates a printer interface so that the system appears as a printer resource when connected to the report source. The controller receives a report, and using positional and/or reference cues contained in the report, obtains identifying information as to intended report recipients. The identifying information is used to look up destination information relating to the recipient, such as the recipient's facsimile machine telephone number, in a database. The controller is automatically operative to queue the report, after stripping printer control and escape codes, for transmission to the intended recipient, utilizing a facsimile machine, fax board, or other data communications device connected to the controller.

34 Claims, 11 Drawing Sheets

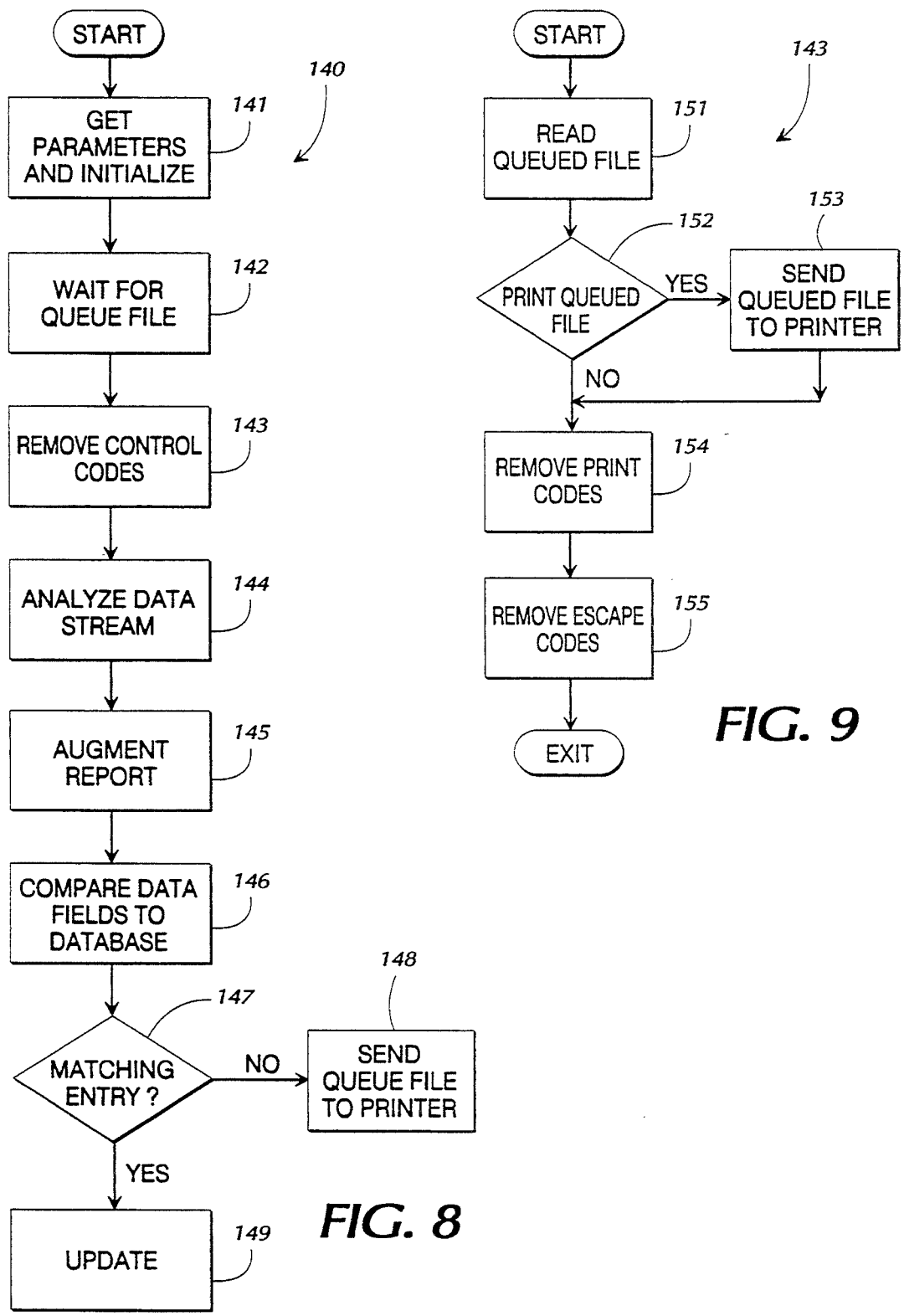

SELECTIVE COMPUTER-GENERATED INFORMATION DISTRIBUTION SYSTEM BY COMPUTER PERIPHERAL EMULATION AND USE

TECHNICAL FIELD

The present invention relates generally to information distribution through computer peripheral devices. More particularly, the present invention relates to a system which selectively distributes computer-generated information such as laboratory reports by emulating a computer peripheral and disseminating the information via peripheral devices such as modems, facsimile machines, and the like.

BACKGROUND OF THE INVENTION

Computers, especially personal computers, have made possible the quick and efficient processing of large amounts of data for large and small businesses, commercial establishments, manufacturing facilities, medical service centers, educational institutions as well as individuals. However, the delivery and distribution of such computer-originated information or reports to interested parties or recipients lags far behind the speed of processing. Generally, the distribution of computer reports has been limited to conventional methods such as the delivery of paper copies of the reports through interoffice mail, personal couriers, overnight delivery services or the United States Postal Service. The reports also have been passed on through oral communication including telephone reports. More recently, computer reports have been delivered through facsimile transmission and through computer system services including a modem. Nonetheless, all of these distribution systems share common problems in the delay of information and report delivery and the labor intensive aspects of the delivery.

In particular, information may be processed by computer in a matter of minutes, but the computer reports must be reviewed by an individual to determine delivery information including the manner of distribution, the identity of the recipient of the report or other recipient, the addresses of report recipients or other recipients, and other pertinent information. Such personal attention to each report is time consuming, thereby increasing the cost of the report as well as delaying its delivery. The high costs and delays in delivering computer reports are a factor in many businesses and institutions such as: stock and bond brokers, who use computers to trade in stocks and bonds as well as prepare reports on such trading for clients; insurance salespersons, who report purchases of insurance or other information to customers; and schools and universities, which compile test scores and other grading information by computer and provide grade reports to students.

A medical service center such as a hospital is a good example demonstrating the problems of delivering computer reports quickly and efficiently. A battery of tests and laboratory procedures are available to the physician to aid in diagnosing illness and injury and in prescribing methods of treatment. Often, such medical tests are performed in the hospital or affiliated laboratories. The results are computer-processed and the reports of such test results have to be distributed to physicians who have offices located off the hospital campus. In addition to test reports, physicians receive factual information relating to patients such as the hospital's face sheets, which contain patient billing and other identifying information. The quicker the test reports and other materials are distributed to the physician, the quicker the physician may reach a diagnosis and begin a course of treatment. Thus, quicker distribution of test reports is related directly to improved patient care. Quick delivery of patient billing information allows for speedier processing of patient accounts.

Delays in the distribution of test reports and other materials are inherent given the off hospital campus location of most physicians' offices. Even within the hospital, the delivery of test reports may be delayed depending upon the information distribution network of the hospital. The practice of many hospital laboratories is to telephone the physician's office and leave a message regarding the availability of the test reports. If the situation is extremely urgent, the test reports may be communicated over the telephone by lab personnel to the physician or the physician's support staff. If urgent, the physician or a courier may stop by the hospital lab and pick up the test reports. In other cases, the test reports may be provided by facsimile transmission or may be mailed to the physician. Patient billing information may be delayed or otherwise separated from the test reports.

In all of these cases, hospital or laboratory personnel are required to correlate the test reports or other materials with a particular patient and with one or more physicians, make and file copies of the test reports and materials, and forward the test reports and materials to the physicians or other recipients. Forwarding such information involves quite a bit of time-consuming administrative work, which cuts into hospital and laboratory efficiency. For example, when the lab forwards the test reports by telephone, lab personnel must have the physician's telephone numbers and track the physician amongst various locations or repeatedly call until the reports are delivered. Faxing test results to the physician requires lab personnel to have the physician's fax number, to have a fax machine or access thereto, and to see that the fax goes through to the correct destination with the test reports. Even when the test reports are only mailed to the physician, the test reports must be enclosed in a properly addressed envelope with the correct amount of postage. The weighted cost of a pulling a short test report, stuffing the envelope, addressing the envelope, and applying postage is approximately $1.18, according to recent information. In a hospital laboratory which processes 500–700 laboratory test reports on a daily basis, processing the test reports by mail is a daily administrative expense of $590–$826. More time consuming methods of processing the test reports significantly increase this daily expense.

Unfortunately, there is little a physician can do under the prior art systems in speeding the delivery of test reports or other patient materials. As noted, the physician or one of the physician's staff may pick up the test reports at the laboratory when the reports or information are available and when the schedule of the physician or the courier permits. However, physicians have to depend on contact from the hospital or lab indicating the information or test reports are ready for pick up. The alternative is to repeatedly contact hospital or lab personnel in person or by telephone with inquiries as to the status of the information.

There are prior art systems which provide for the delivery of test reports from the laboratory to the physician through the use of networked computers and peripheral devices. One prior art system known as the PRACTI-COM system (manufacturer unknown) operates by downloading test reports from a laboratory's computer system directly via modem to a physician's computer system. There are significant drawbacks to these types of prior art distribution systems. First, these prior art systems require that both the laboratory and the physician's office are equipped with computers. This can be a significant expense for the lab and for the physician. Second, these systems require communication capability between the laboratory's computer system and the physician's computer system. The establishment of such communication capability also can be a significant expense, and the existence of so many different computer communications networks and protocols complicates matters. Third, these prior art distribution systems generally require the participation of a trained computer operator within the physician's offices.

In order to retrieve test reports from the laboratory's computer using the prior art distribution system, the physician's computer operator attempts to make a connection between the lab's computer and the physician's computer via a modem. If the operator is unsuccessful in connecting to the laboratory's computer, the operator has to hang up or disconnect the modem, and attempt to make the connection later. Obviously, repeated attempts at connection to the lab's computer delay transmission of test reports. If the connection attempt is successful, the operator must access the test results file designated for the physician and check if the test reports are available. If ready, the test reports are downloaded to the physician's computer. The operator must then print the test reports and provide them to the physician.

The necessity of an operator in the physician's office is a significant drawback to these types of prior art systems. Ordinarily, physician's offices are staffed only during office hours. Thus, lab reports can only be accessed during these limited times when an operator is present, thereby delaying the delivery of the test reports to the physician. In addition, the necessity of employing an operator with computer skills may be cost prohibitive, with the result that the physician's medical staff has to be diverted from medical duties to retrieve test reports.

Although a hospital/physician scenario has been used to describe the problems of delivering computer reports quickly and efficiently, these problems are not confined to medical service centers. Other businesses, institutions, and manufacturing facilities that are sources of computer report generation face the same sort of problems in the distribution of such information.

Accordingly, there is a need for an information distribution system which provides recipients or other recipients with computer reports as quickly and cost effectively as possible. In particular, there is a need for an information distribution system that provides a physician with laboratory test results and other patient information as quickly as possible in order to improve patient care, and that minimizes the time, number of personnel, and amount of equipment necessary to the distribution of such information.

SUMMARY OF THE INVENTION

As will be seen, the present invention satisfies the foregoing criteria. Stated generally, the present invention provides a method for distributing reports received from a data processing system including at least one report source where the reports are provided in a digital data stream having data fields corresponding to a predetermined peripheral device protocol. The method of the present invention includes the steps of receiving the data stream corresponding to the report from at least one report source; reading a selected data field from the report; comparing the selected data field with at least one entry in a database to find a matching database entry corresponding to the selected data field; in response to finding the matching database entry, providing destination information for the report from the matching database entry; and in response to the provision of destination information, distributing the report to the destination corresponding to the destination information, whereby the report is distributed to the report recipient.

In addition, the present invention provides an apparatus for distributing reports received from a data processing system including at least one report source where reports are provided in a digital data stream having data fields corresponding to a predetermined peripheral device protocol. Stated generally, the apparatus of the present invention includes: data processing interface means for connecting the apparatus to a data processing system associated with at least one report source; a system controller operative to accept the data stream from the source via the data processing network interface means; reading means associated with the system controller for reading a selected data field of the data stream; at least one database having database entries with destination information; comparison means associated with the system controller for comparing the selected data fields with at least one of the database entries, the comparison means being operative to find a matching database entry corresponding to the selected data field; destination provision means associated with the system controller for providing destination information for the report from the matching database entry; and distribution means responsive to receipt of the destination information for distributing the report to the destination, whereby the report is distributed to the report recipient.

The method finds particular utility in applications where reports are generated by data processing devices such as personal computers (PC) or laboratory equipment and intended to be printed by a printer, and especially when such personal computers or laboratory equipment are attached to a data communications network. The method may be implemented as a program for a microcomputer-based apparatus comprising at least one input port, at least one output port, and a database, where the input port is connected either directly or via a network interface to a report-generating PC or laboratory equipment, and the output port is connected to at least one facsimile or "fax" modem and a telephone line. The program is operative for causing the microcomputer-based apparatus to receive a print file from the report-generating PC or laboratory equipment formatted in one of the many known printer file protocols, so that the microcomputer-based apparatus effectively appears to be a "printer" to the report-generating PC or laboratory equipment. The program is further operative for examining the print file for the presence of predetermined identifying indicia, and carrying out the steps of the method for locating destination information for a given report contained in the database. The program is then further operative for processing the print file as a facsimile or "fax" message using a facsimile program and the fax board. The report is then automatically transmitted, for distribution, via the fax modem to one or more destinations identified in the method as intended recipients of the report.

The present invention enables computer-generated or computer-processed reports to be distributed quickly, efficiently, and cost effectively. The result is improved service to the report recipients, who in turn, can act more quickly based on the timely distribution of such reports. With regard to the preferred embodiment, the present invention enables the hospital, laboratory and physician to provide better patient care by delivering test results and other information to the physician as quickly as possible, often by facsimile. Diagnoses are reached more quickly, and courses of treatment can be started earlier with early receipt of test results.

Advantageously, the present invention saves the time and money of the report generating source whether it is a stock brokerage, insurance agency or school system. The present invention minimizes staff requirements by obviating administrative work in mailing, manually faxing, or otherwise delivering the computer reports under the prior art systems. In particular, hospital and laboratory staff requirements are minimized. Because the present invention provides test results directly from the lab's computer to the physician's fax machine or printer, hospital and lab staff do not have to manually fax or mail test results or waste time and effort telephoning physicians' offices regarding the availability of test results. Also, the direct delivery capability of the present invention relieves lab staff from information distribution duties, thereby allowing them time for other work.

In addition, the present invention saves money in terms of equipment and information distribution costs. With the present invention, the report generating source does not have to have a scanning-type fax machine or need to incur mailing expenses such as stationery, postage, or high cost couriers. According to one aspect, a system constructed in accordance with the present invention may be attached to and function as part of a computer network, rather than a stand-alone system, effectively appearing as a "printer" resource to the report generating source. Advantageously, such operation obviates any changes in the report source's software. Thus, development expenses are kept to a minimum.

In particular, the efficiency and capability of the present invention in linking the hospital and the physician's office draws physician referrals. Test results and other documents received by the present invention can be automatically stored permanently (archived) and made available anytime they are needed. The ability for automatic and unattended archival of test reports in and of itself is a significant advantage of the present invention. The present invention can be configured to link multiple departments within a hospital or a laboratory, and consulting physicians can be linked to general physicians without the necessity of a computer system located in each linked office. The present invention offers a secure distribution system for test results including full confirmation of receipt with permanent audit trail.

The present invention provides report recipients and recipients with quick distribution of reports and gives them the opportunity to act more quickly on the reports. From the physician's standpoint, the present invention enables the physician to provide better patient care and to also save time and money. Of paramount importance, patients are better served when test results are received more quickly. With the present invention, the average time that it takes to send many short reports from the hospital or laboratory to the physician's office is under a minute. In other words, test results are in the physician's hands almost immediately upon their completion. Physicians can follow up faster on test results and order more tests if necessary. There is no time wasted by the physician or staff in checking on the status of test results, or in making special trips to pick up test results.

The present invention minimizes equipment requirements. The present invention does not require that report recipients or recipients have a computer system in the office, but only a common fax machine. Surveys indicate that 40–55% of physicians already have fax machines in their offices. The present invention may be configured readily with the physician's office management system.

Therefore, it is an object of the present invention to provide an improved information distribution system.

It is also an objection of the present invention to provide an information distribution system that selectively distributes computer-generated information by simulating a computer peripheral and disseminating the information to a plurality of connected peripheral devices such as modems, facsimile machines, and the like.

It is another object of the present invention to provide an information distribution system that distributes computer-generated reports quickly, efficiently, and cost effectively.

It is another object of the present invention to provide an information distribution system that distributes computer-generated reports automatically to report recipients and other recipients.

It is another object of the present invention to provide an information distribution system that is able to scan or monitor a digital data stream corresponding to a computer-generated report for positional or reference cues indicating data fields, to compare such data fields with entries in a database to find destination information, and to automatically distribute the report to the destination via a communication means such as a fax modem.

It is a further object of the present invention to provide an information distribution system that enables a physician to provide better patient care because of more rapid receipt and handling of laboratory test results.

It is also an object of the present invention to provide an information distribution system that provides delivery of test results or other patient information into the hands of the physician almost immediately upon completion of the generation of test results or other information.

It is another object of the present invention to provide an information distribution system that automatically provides test results or other patient information from the hospital or laboratory to the physician.

It is yet another object of the present invention to provide an information distribution system that relieves the hospital or laboratory staff from direct participation in transmitting, mailing, or delivering test results or other patient information.

It is a further object of the present invention to provide an information distribution system that minimizes mailing expenses such as administrative expense and stationery, postage or courier costs.

It is also an object of the present invention to provide an information distribution system that is compatible with existing computer and network communication systems in hospitals, laboratories, and physicians' offices.

It is another object of the present invention to provide an information distribution system that may be used in connection with the software of existing report-generating systems within hospitals, laboratories, or physicians' offices.

It is yet another object of the present invention to provide an information distribution system that minimizes the equipment and software development expenses of a hospital, laboratory, or physician's office.

It is also object of the present invention to provide an information distribution system that can store or archive test results and other documents permanently and that can retrieve such information as necessary.

It is another object of the present invention to provide an information distribution system that can link multiple departments within a hospital or a laboratory for distribution of laboratory test results.

It is also an object of the present invention to provide an information distribution system that can keep statistical records regarding the type and number test results and other patient information distributed from the hospital or laboratory to other departments, to physicians, or to other recipients.

It is yet another object of the present invention to provide an information distribution system that can link consulting or referring physicians with general physicians for the distribution of laboratory test results or patient information without the necessity of a computer system located in each physician's offices.

It is a further object of the present invention to provide an information distribution system that offers a secure method of distributing test results or other patient information.

It is also an object of the present invention to provide an information distribution system that relieves a physician's staff from wasting time and effort in checking the status of test results or other patient information.

It is another object of the present invention to provide an information distribution system that relieves a physician's staff from computer duties in attempting to access test results or other information in a hospital or laboratory's computer.

It is yet another object of the present invention to provide an information distribution system that obviates the necessity of a computer system in a physician's office for the purpose of receiving test results or other information.

It is a further object of the present invention to provide an information distribution system that minimizes the amount of equipment necessary to receive test results or other information in a physician's office.

It is also an object of the present invention to provide an information distribution system that can distribute test results to a fax machine in a physician's office.

That the present invention and the preferred embodiment thereof overcome the drawbacks set forth above and accomplish the objects of the invention set forth herein will become apparent from the detailed description of the preferred embodiment to follow.

BRIEF DESCRIPTION OF THE DRAWINGS

FIGS. 6–13 are flow charts illustrating steps of particular method(s) of operation of the preferred embodiment of the present invention, including the elements of the software modules of FIG. 5.

DETAILED DESCRIPTION OF THE PREFERRED EMBODIMENT

Figure 2:
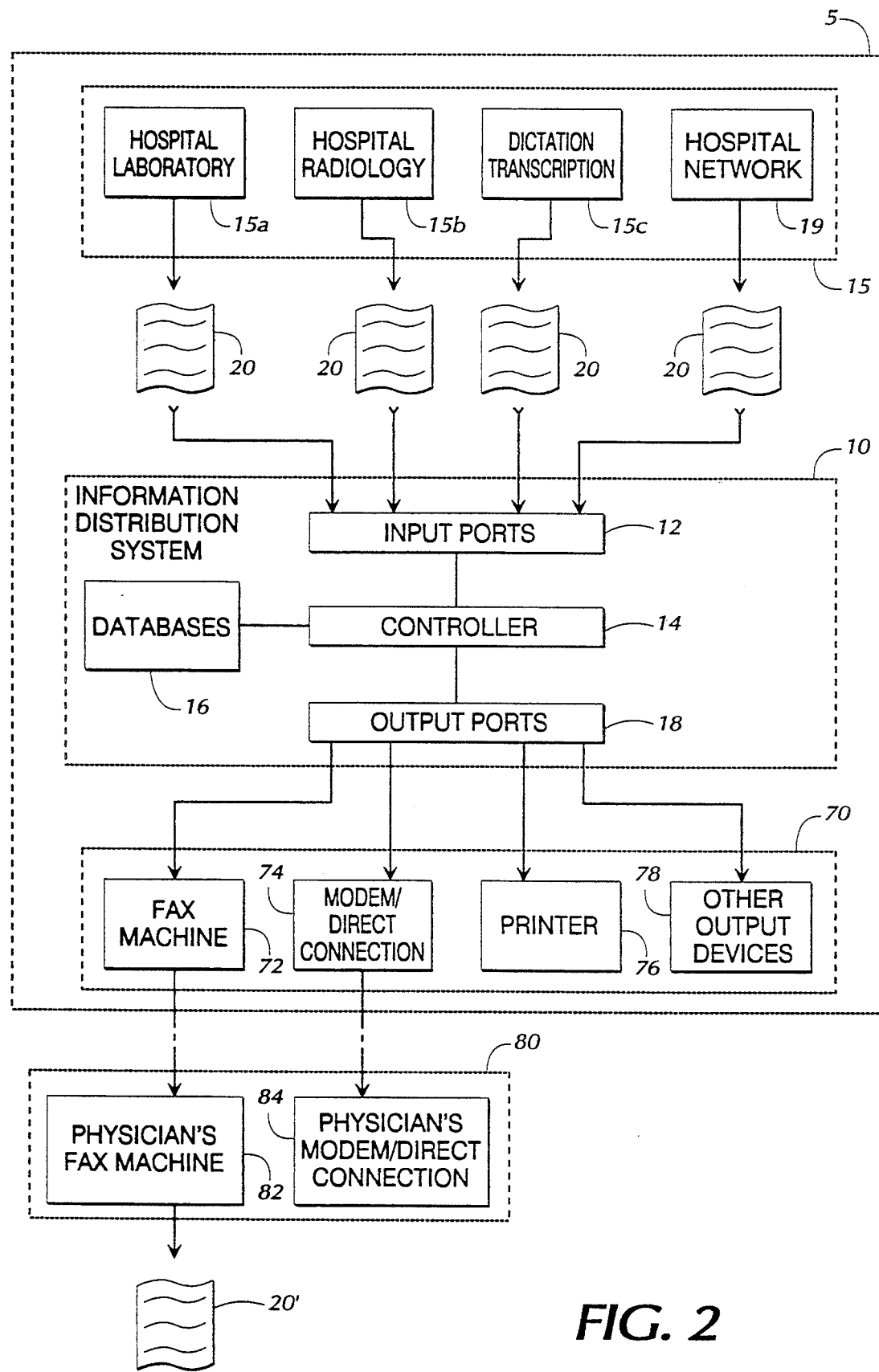
FIG. 2 is a block diagram illustrating the preferred environment of the preferred embodiment of the present invention.

Referring now to the drawings, in which like numerals indicate like elements throughout the several figures, the preferred embodiment of the present invention is described in the context of an information distribution system 10 shown in FIG. 2 used to distribute reports 20 or other information generated by sources 15 within a hospital to physicians practicing at that hospital. However, the present invention may be used in other institutional and business settings for report distribution such as, inter alia, an insurance firm, stock brokerage, schools, universities, etc. By way of brief introduction but not limitation, the present invention reads a selected data field from a report generated by a source, and compares the selected data field to database entries corresponding to the selected data field to find a matching database entry. Destination information for the report is provided by the matching database entry, and the report is distributed pursuant to the destination information via a communication means.

Figure 1:
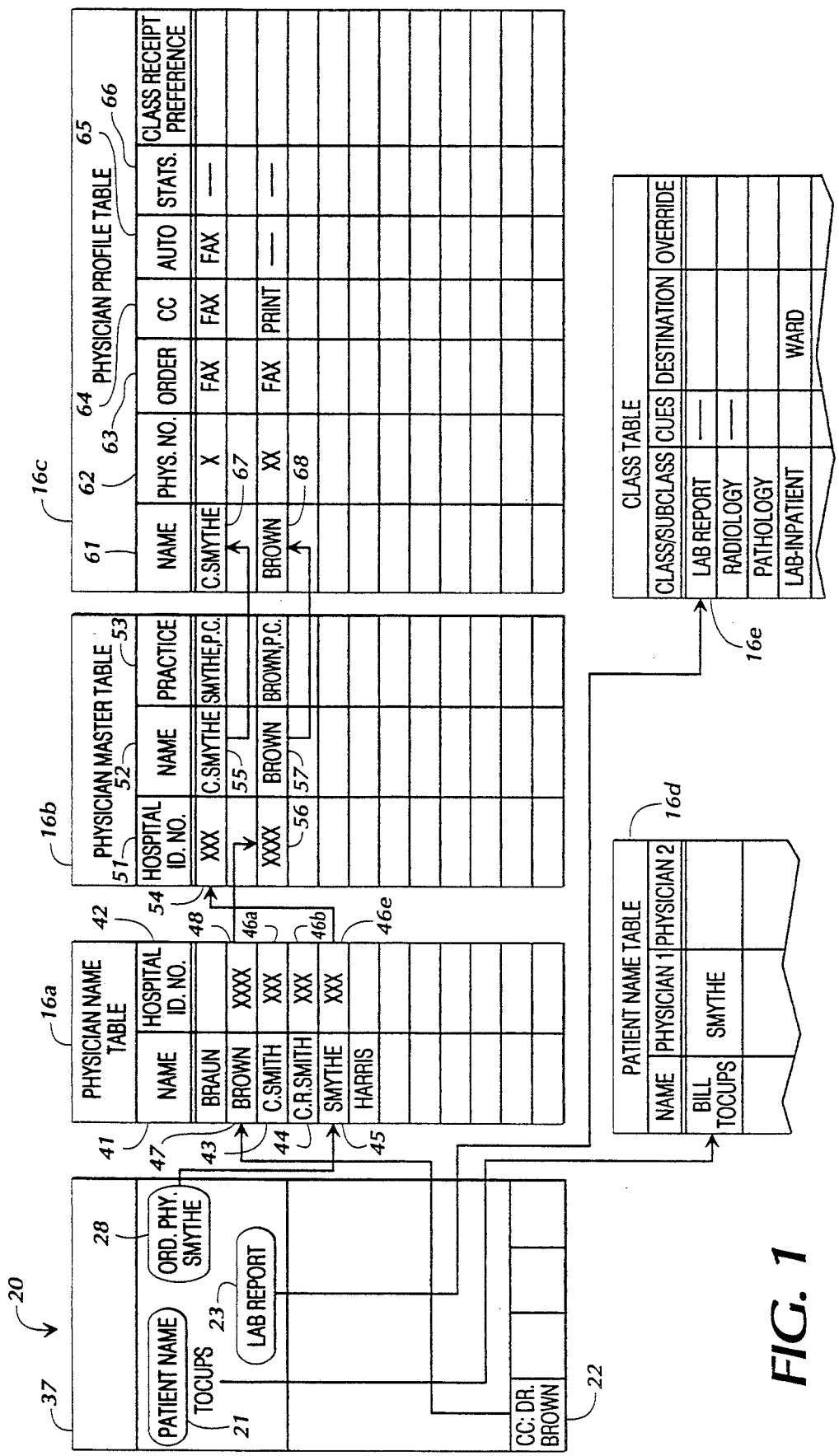
FIG. 1 is a block diagram illustrating a representational report and databases relating to the preferred embodiment of the present invention.

Prior to describing the preferred embodiment of an information system 10 constructed in accordance with the present invention, and the steps of methods carried out in such preferred embodiment, there will be provided some necessary background as to the construction and contents of exemplary reports and exemplary report recipients, to illustrate a typical application of the present invention in the context of a hospital or laboratory setting. FIG. 1 illustrates a generalized report 20 such as may be used by a hospital laboratory in reporting the results of medical tests. FIG. 1 also illustrates representational databases 16 maintained in a computer system constructed in accordance with the disclosed embodiment, having entries relating to physician identification, report destination and other information. In the preferred embodiment, a plurality of interrelated databases are used to store and provide the information necessary for the distribution of hospital reports and other information.

Five databases 16 are illustrated in FIG. 1. A physician name table 16a contains entries for names 41 of physicians, who may be intended recipients of reports distributed through the present invention, and hospital identification numbers 42 corresponding to each physician name entry. Preferably, variant spellings or identifiers of a particular physician are entered as individual entries in the physician name table 16a. Thus, as illustrated in FIG. 1, there are three entries for "Dr Smythe" in physician name table 16a., including "C. Smith" 43, "C. R. Smith" 44, and "Smythe" 45. In this example, all three of these entries have the same corresponding hospital identification number 46 for Dr. Smythe, indicating that all three variants correspond to the same individual report recipient. In this way, a report destined for Dr. Smythe is distributed as quickly as possible despite the variations in the spelling or identification of Dr. Smythe in the data field of the report.

A second database illustrated in FIG. 1 is the physician master table 16b, which preferably includes an entry for each physician corresponding to hospital identification number 51, name 52, and and practice affiliation 53. A third database illustrated in FIG. 1 is the physician profile table 16c, which includes information relating to a physician's preferences as to the receipt of reports, as well as physician identifying information such as physician name 61 and physician number 62.

Generally in the preferred embodiment, a report recipient may receive a report due to his or her membership in one of at least three different recipient categories—as an ordering recipient, a carbon copy ("cc") recipient, or an automatic copy ("auto") recipient. In the hospital example shown in FIG. 1, the recipients are generally physicians. Thus, an ordering physician is the physician who placed the order for the report, such as Dr. Smythe, whose name appears in an "ordering physician" field 28 shown on the report 20 in FIG. 1. A "cc" physician is an associated physician or other attending physician designated to receive a copy of the report. In the preferred embodiment, a physician designated as "auto" physician automatically receives a copy of a report relating to a particular patient, without regard to whether the physician ordered a test or is an indicated cc recipient. The "auto" designation is particularly useful in connection with patient referrals from one locality to another.

The physician profile table 16c maintains information relating to a physician's preferred mode of report distribution based upon the designation of the physician as an ordering physician 63, a "cc" physician 64 or an "auto" physician 65. Thus, as shown in FIG. 1 in connection with Dr. Smythe's database entry 67 in the physician profile table 16c, a physician may receive all reports by fax no matter the physician designation. Or, as shown in connection with Dr. Brown 68, a physician may receive ordering physician reports by fax, and "cc" physician reports by printed copy, and prefer not to receive auto physician reports.

The physician profile table 16c also contains report destination information such as facsimile transmission numbers or print codes corresponding to each physician entry in accordance with the physician's receipt preferences. Further, the physician profile table 16c includes statistical entries 66 for use in maintaining and servicing the disclosed embodiment, or for use in monitoring the types and number of reports distributed.

Other databases may be employed in the present invention to implement related features, or provide additional cross-indexing capability. For example, a patient table 16d in FIG. 1 provides a cross-reference by patient name to one or more associated physicians, so that a report recipient who for some reason cannot be identified through the normal procedure of looking up ordering physician, cc physician, or auto physician, can receive a report because of association with a particular patient. Other tables or databases (not shown) may be provided to relate physicians to their practice affiliations. A practice table (not shown) includes entries for the names of physicians' practices affiliated with the hospital, the names of the physicians in the practice, the telephone numbers and fax numbers of the practice offices, as well as statistical information. This permits a particular physician to be identified, and receive his or her reports, when only a practice name is provided on a report.

A practice profile table (not shown) is similar to the physician profile table 16c. The practice profile table includes entries for the names of the affiliated practices, practice numbers, statistical information, and information relating to the preferred mode of receipt of reports.

A class database or table 16e contains information as to particular classes and subclasses of reports, and enables the provision of special handling and other features for particular classes of reports, or subclasses of a given class of reports. For example, "lab reports" may be a certain class of reports, while "pathology" may be a different class that is handled differently under certain conditions such as archival to a different archival drive. The class table also generally contains positional and/or reference cue information that facilitates the identification of intended recipients and proper handling. A destination override field provides that certain classes or subclasses may be sent to particular locations, or that destinations associated with particular physicians overridden under certain conditions. For example, a report of the "lab report" class, but with additional subclass identifying indicia (see field 26 in FIG. 4) that the particular patient is an inpatient, can be sent directly to a ward or nurse's station fax machine, to override the normal ordering physician entry that the report should be sent to the physician's office. This provides additional flexibility in directing reports to locations where they are urgently needed, without having to reconfigure the system for different fax numbers for physicians who may work at more than one hospital.

All of the databases, such as the tables 16a-16e are preferably constructed as relational databases maintained and stored on a computer system that carries out the steps of the methods described herein (see FIG. 2), although flat file and other types of databases can also be utilized.

With the understanding now that the databases 16a-16e are constructed as described above, the preferred embodiment reads a selected data field in the report 20, such as the identification of the ordering physician Smythe 28, and compares the data field to entries in a database such as physician name table 16a. The Smythe data field 28 corresponds to the Smythe entry 45 and hospital ID no. XXX entry 46c in the physician name table 16a. The hospital ID no. XXX entry 46c corresponds to the hospital ID no. entry 54, and to the C. Smythe entry 55 in the physician master table 16a. The C. Smythe entry 55 is used as an entry point to the physician profile table 16c, which includes an entry 67 for C. Smythe, as well as other entries relating to report distribution information.

Similarly, the data field 22 for "cc" physician Dr. Brown is matched to the entry 47 for Brown in physician name table 16a. The corresponding entry 48 for Brown's hospital ID no. XXXX is matched to the hospital ID no. XXXX entry 56 and to Brown entry 57 in the physician master table 16b. The Brown entry 57 is used as an entry point into the physician profile table 16c, which includes an entry for Brown 68 as well as other entries relating to report distribution information.

Figure 3A:
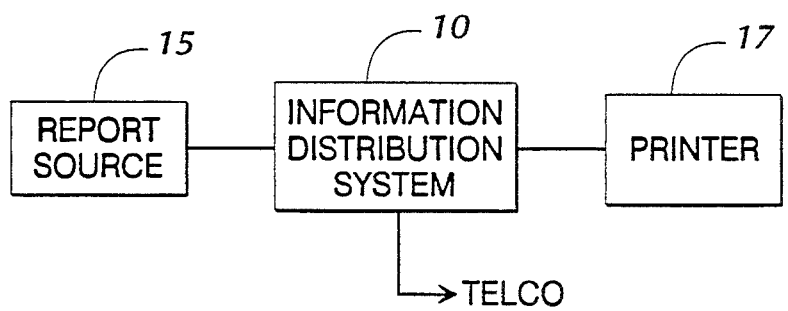
FIG. 3, consisting of FIGS. 3A–3C, is a block diagram illustrating various connection alternatives for the preferred information distribution system to report sources.

Generally, an information distribution system constructed in accordance with the present invention may interface with a report-generating source or sources in one of at least three ways. Referring in this regard to FIG. 3A, the information distribution system 10 may be set up in-line or in series between a report source 15 and an associated printer or print station 17. In such an arrangement, the information distribution system 10 effectively intercepts printer traffic generated by the report source and directly transmits the report in the manner described herein. The system 10 may under some conditions pass the report print file to the printer 17 for printing in the usual manner, for example, the system may be set up to print on the printer 17 for a "file" copy.

Figure 3B:
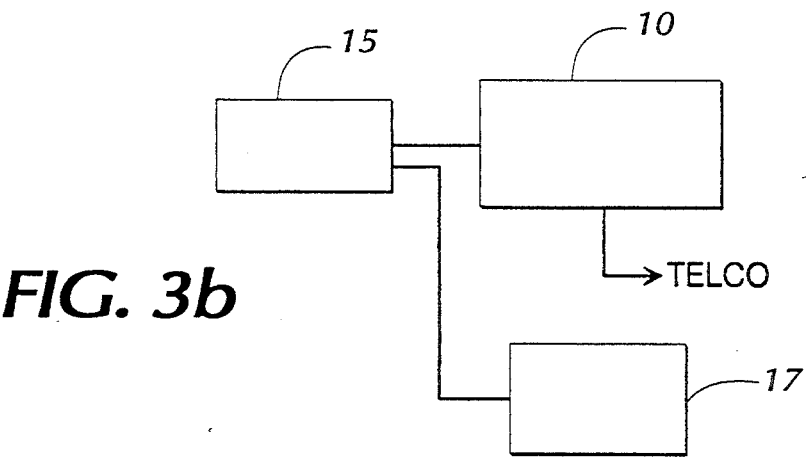

Or, as shown in FIG. 3B the information distribution system 10 may be set up in parallel with the print station 17 of a source. In a parallel arrangement, it would normally be expected that the printer 17 would print the report in the normal course of operations, but that the system 10 would also distribute the report to certain intended report recipients in the manner herein described.

Figure 3C:
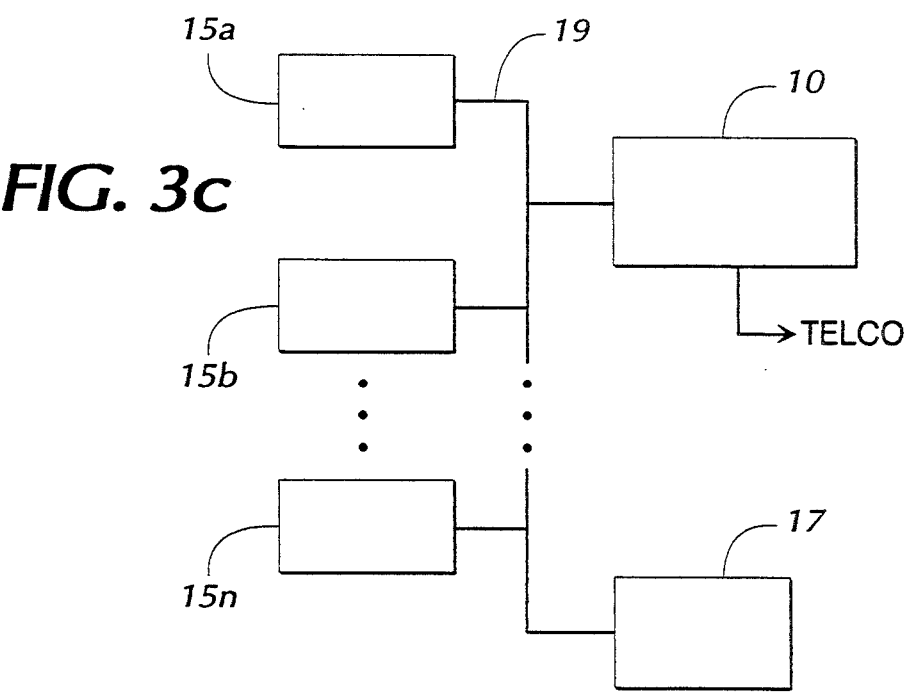

As shown in FIG. 3C, the information distribution system 10 may operate as a networked device on a network 19 of sources 15a, 15b, . . . 15c. In such a networked arrangement, the system 10 would preferably appear and behave as a printer resource on the network.

The information distribution system 10 is preferably configured as a stand-alone peripheral device, but it may also be configured on a card for insertion and operation on any central processing unit ("CPU") as necessary.

With the foregoing background now in mind, please turn to FIG. 2 for a discussion of how the preferred embodiment receives reports generated in the form of a digital data stream from the source or sources formatted in accordance with a predetermined peripheral device protocol. In FIG. 2, the information distribution system 10 of the present invention is illustrated in its preferred environment of a hospital report distribution system 5. Preferably, information distribution system 10 is connected to a plurality of sources 15. Each connection may be of a different type. Sources 15 may include, inter alia, the hospital laboratory 15a, the hospital radiology department 15b, or the dictation-transcription department 15c. All of these sources prepare or process computer-generated reports such as laboratory test results or reports, or patient accounting information commonly referred to as "face sheets".

The report sources 15 in FIG. 2 are generally computer-based devices having at least one printer port operative for providing a digital data stream formatted in a known printer protocol, and are connectable via industry standard printer cables to output or distribution devices 70, including printer 76. The preferred information distribution system 10 supports asynchronous print format receiver connections and 3270 print station receiver connections, and as shown in FIG. 3A and FIG. 2, may be connected in series between the report sources 15 and the printer 76.

The information distribution system 10 may also be connected to a communications network 19, such as an ETHERNET, Token-Ring or other known local area network schemes and protocols. Or, the information distribution system 10 may be connected to a source via a modem.

As shown in FIG. 2, the preferred information distribution system 10 has a data processing interface comprising a plurality of input ports 12 for connecting to sources 15, a controller 14 for processing the reports received from sources 15 in conjunction with databases 16, and an interface such as a plurality of output ports 18 for connecting to distribution devices 70. The system controller 14 in the preferred embodiment is constructed around a microcomputer-based system such as a tower microcomputer unit with an Intel Corporation 386/486 or equivalent microprocessor, having a 200 MB or larger hard disk and console CRT, using the UNIX/XENIX operating system. The preferred embodiment also makes use of two fax boards such as a model JT-FAX 9600B fax board manufactured by Hayes Microcomputer Products, Inc., Norcross, Ga., which are Group 3 compatible, and an MNP compression type 2400/9600 baud modem for software support.

The connection of the data processing interface input ports 12 to the sources 15 and output ports 18 to distribution devices 70 is well known to those skilled in the art. For providing the input ports 12 and output ports 18, the preferred embodiment utilizes a DIGIBOARD model PC/Xi multiport controller serial interface card having sixteen input/output ports, manufactured by Digiboard of Eden Prairie, Minn., as an input/output interface. Of the sixteen lines of the preferred serial interface card, four are devoted to input, three are devoted to output, two are devoted to fax lines, and one line is devoted to a printer connection. The configuration of the preferred embodiment supports up to four multiport serial interface cards, which allows for up to sixty-four input/output devices.

The system controller 14 operates to accept a data stream from one or more of the sources 15 via the data processing interface such as the input ports 12. In addition, the controller 14 operates to read selected data fields of the data stream, to compare the selected data fields with database entries in an associated database 16 for a matching database entry corresponding to the selected data fields, to provide destination information for the report from the matching database entry, and to direct the report to output ports 18 for distribution to report recipients.

The output ports 18 of the present invention constitute a data processing interface such as is well known to those skilled in the art with a connection to miscellaneous well known report distribution devices 70 such as, in the preferred embodiment, a fax machine 72, modem/direct connection 74, printer 76, or other output devices 78. Distribution of the reports through other output devices 78 also may include distribution of the reports to an optical disk storage system or other data storage device, for archival purposes. As directed by the controller 14, reports are output for distribution through the output ports 18 to the report distribution devices 70.

Also as illustrated in FIG. 2, the report distribution devices 70 distribute the reports to recipient distribution devices 80 such as a fax machine 82 or a modem/direct connection 84. Possible methods of transmission of the reports include compressed blocked data (CBD), print image (PI), and facsimile transmission. The CBD format is used for the transfer of data to the recipient's computer which then can be inserted into a practice management system. The PI format is used for directly printing the information at the recipient's location. Preferably, however, the report distribution devices 70 deliver reports automatically to the physician or other recipient by way of the fax machine 82 located in the physician's office.

Thus, in the preferred embodiment, a report 20 prepared by a report generating source such as the hospital laboratory 15a is transmitted via a digital data stream to the data processing interface such as input ports 12 of the system 10. The system controller 14 operates to accept the data stream and to find destination information relating to the report through a comparison of selected data fields in the report to database entries having destination information corresponding to the selected data fields. The system controller 14 then directs the data stream comprising the report to one of the output ports 18. The report 20 is thus directed to a report distribution device such as a fax machine 72, which, in turn, transmits the report 20 to a recipient distribution device such as a physician's fax machine 82. The physician then receives a facsimile copy 20' of the report. In this way, the report is delivered automatically to the report recipient without the necessity of human intervention, thereby saving time and money.

Figure 4:
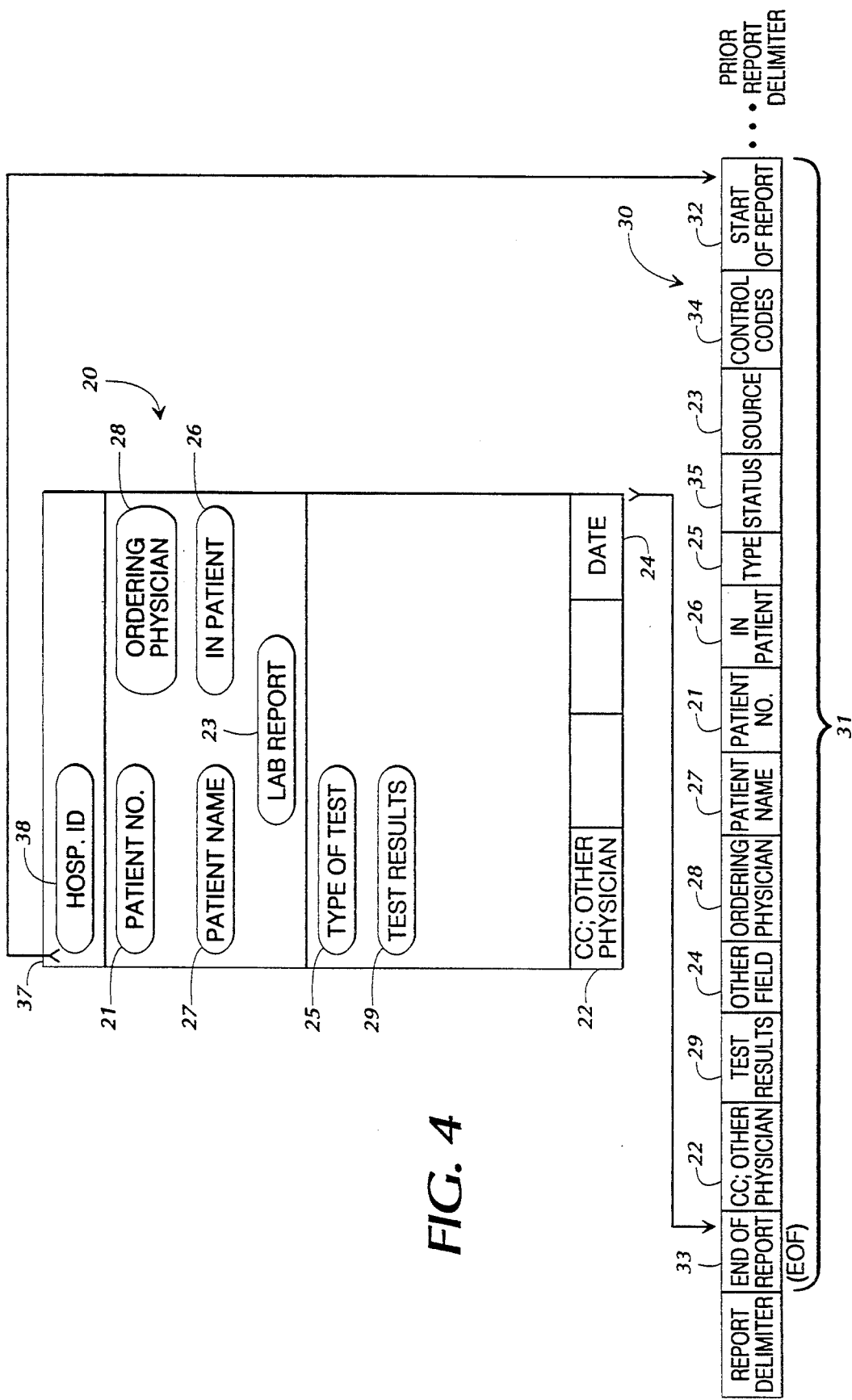
FIG. 4 illustrates an exemplary report and a corresponding digital data stream corresponding to the exemplary report that is distributed by the preferred embodiment of the present invention.

FIG. 4 illustrates a generalized exemplary report 20 such as may be used by a hospital laboratory in reporting the results of medical tests. Similar reports are generated by other businesses and institutions such as, inter alia, stock brokerages, insurance companies, schools and universities, etc. although with different subject matter. Generally, a report 20 contains identification indicia or information relating to the patient no. 21, the names of physicians or recipients 22 of the report, the report's source 23, a date 24, type 25, in/out patient status 26, patient name 27, the name of the ordering physician 28, and test results 29. It will be understood that each of these fields or indicia comprise strings of ASCII characters embedded in a predetermined data communications format corresponding to a printer protocol or format that a printing device can respond to and print. However, the physical layout or format of the report may differ from hospital to hospital, from laboratory to other hospital department, and even from lab report to lab report. The hospital lab report 20 shown in FIG. 4 is used only as a representative example of computer-generated or processed reports.

Generally, the system classifies and subclassifies reports depending upon certain information contained in the report itself. Thus, report 20 is classified as part of a "lab report" class based upon at least one field of information contained in the report (such as a report title field 23) identifying the report as a lab report, and is subclassified as part of a "lab report, in-patient" subclass based upon information identifying the report as a lab report, as well as upon at least one field of information contained in the report (such as the in-patient indicia 26) identifying the report as pertaining to in-patients. Those skilled in the art will understand that the classification and subclassification of reports can be accomplished by inspecting one or more fields of indicia contained in the report.

The necessity of classifying and subclassifying reports is related directly to the distribution of the reports to recipients. First, a physician may prefer to receive only certain classes or subclasses of reports. This class receipt preference information is maintained in the database 16, namely in the physician profile table 16c discussed in connection with FIG. 1, preferably with one or more database entries associated with the physician indicating whether or not he or she wishes to receive or not receive particular classes or subclasses of reports. Those skilled in the art will understand that this particular described method of report class receipt preference may be implemented via a linking relation established between the physician profile table 16c and the class table 16e, with a receipt/no receipt flag being provided for each class and/or subclass, for each physician.

Second, classification or subclassification information may indicate report distribution recipients and/or locations through correlated information contained in the database 16. Using report 20 of FIG. 4 as an example, a classification of report 20 as belonging to the lab report class, in-patient sub-class, may result in the distribution of report 20 to a fax machine in a particular ward of the hospital. Such an occurrence would be a function of the set-up that reports of a given class (such a lab reports) are to be transmitted directly to a first location for a first subclass (such as to a referring physicians for out-patients), or to a second location for a second subclass (such as to a hospital ward for an in-patient).

Figure 10:
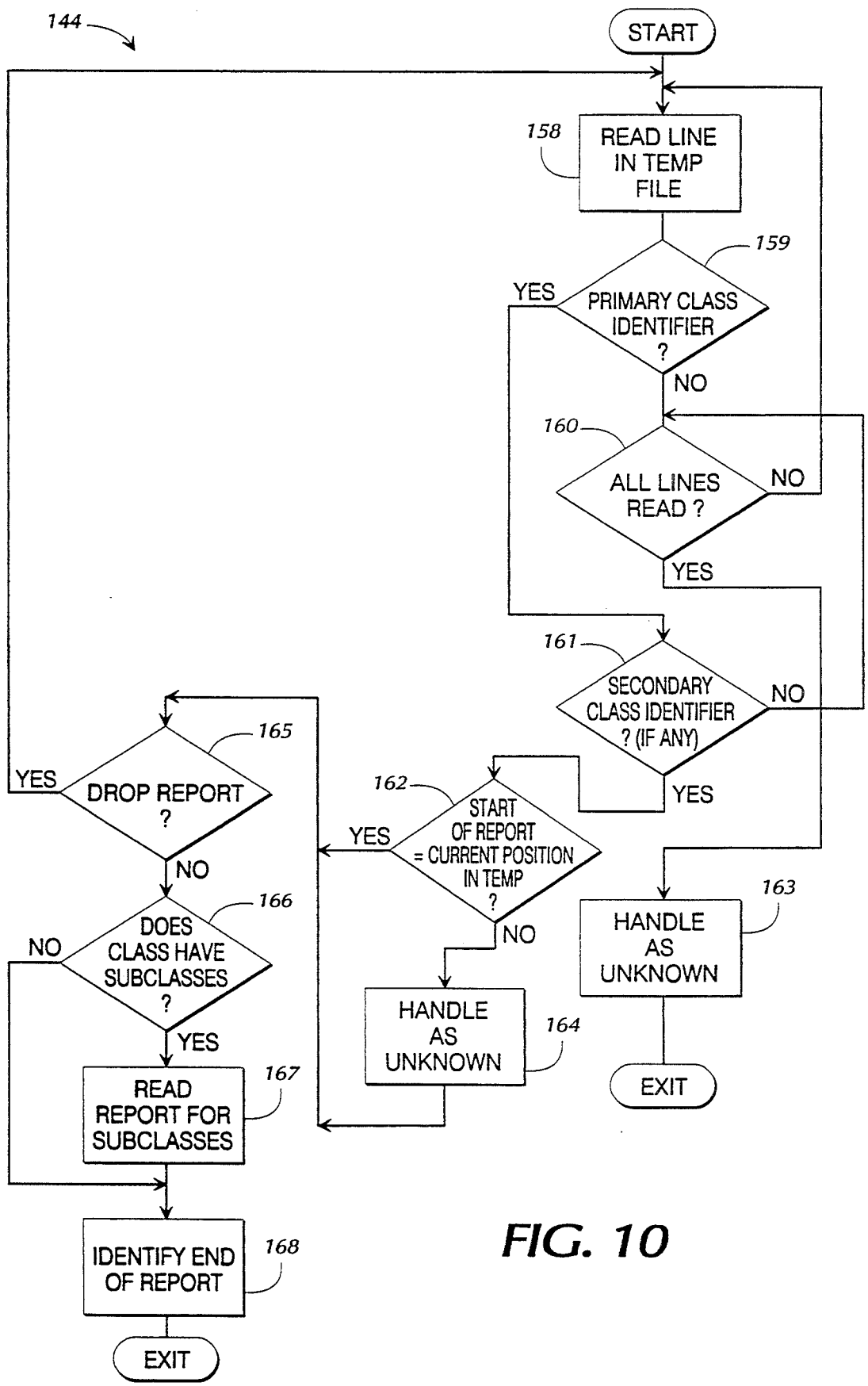

Additional steps relating to the classification and subclassification of reports is provided in connection with FIG. 10.

The report 20 is provided by the report generating source 15 in a digital data stream 30 such as generally represented in FIG. 4. The digital data stream 30 comprises one or more reports. Section 31 of the digital data stream 30 corresponding to report 20 is illustrated for representational purposes in FIG. 4. In particular, digital data stream section 31 will typically include control codes, as is well known to those skilled in the art, for properly formatting the report information for printing purposes. Such control codes include, inter alia, margin set-up, line feed, carriage return, proportional spacing, and the like. Such control codes are a function of a printer protocol; generally so long as positional information is available as to the expected location of certain fields of information on the report for various classes and subclasses of reports, the system 10 is responsive to disregard the control codes.

The digital data stream section 31 in FIG. 4 also includes data fields 21-29 corresponding to the information enumerated above in FIG. 1 as generally contained in a hospital lab report such as patient no. 21, the identity of report recipients 22, source of the report 23, other data fields such as the date 24, the type of the report 25, in/out patient status 26, the patient's name 27, the identity of the ordering physician 28, and the test results 29. In addition, the data stream section 31 may contain a data field identifying the status 35 of the report.

In general, the digital data stream 30 may contain more or fewer information data fields, depending upon the type of report transmitted. The positional order of transmission of particular data fields in a digital data stream varies from report to report, just as the information contained in a report varies. Moreover, there may be more than one class or subclass of reports from each of the sources. For example, a single source may transmit lab reports, face sheets, or informational notices. For purposes of the present invention, the reports are differentiated by class and sub-class classification, and not by report source.

The charts in FIGS. 5–13 provide a detailed description of the method steps executed by the controller 14 in the information distribution system 10. As an analogy to an electrical circuit diagram, these charts are equivalent to a detailed schematic for an electrical circuit where provision of the circuitry for electrical circuit blocks corresponds to provision of actual computer instructions for the chart blocks, in a form suitable for execution by the controller's microprocessor. Thus, the coding of the method steps of these diagrams into instructions of suitable commercially available computers is a mere mechanical step for a routineer skilled in the programming art.

Figure 5:
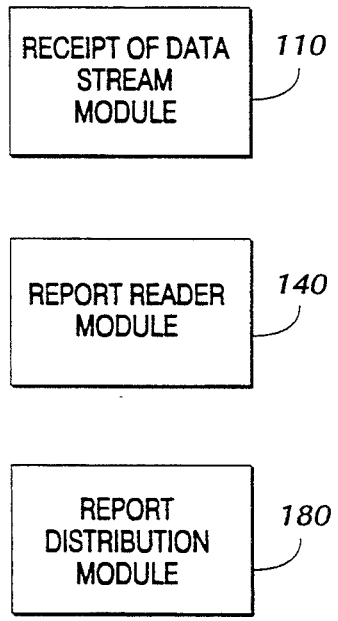
FIG. 5 is illustrates the three principal software modules that carry out the steps of the general method of operation of the preferred embodiment of the present invention.

FIG. 5 is a chart illustrating the general relationship of the methods of operation of the preferred embodiment of the present invention. As will be known to those skilled in the art, modern software programs are often constructed in a modular fashion, with discrete software modules that operate asynchronously with one another, and pass data to each other via data buffers and pointers. In the disclosed embodiment, there is provided a data receipt module 110, a report reader module 140, and a report distribution module 180, each of whose tasks, although related, may be asynchronous due to the different speeds of receipt (input), processing, and distribution (output).

As represented by the receipt of data stream module 110, the information distribution system receives the digital data stream 30 (FIG. 4) corresponding to at least one report from at least one source. Specific steps regarding the receipt of the data stream are presented in connection with FIGS. 6 and 7. As represented by the report reader module 140, the information distribution system reads and processes the reports, whereby destination information is provided for the reports. More specific steps regarding the processing of the data stream are presented in connection with FIGS. 8–12. As represented by the report distribution module 180, the information distribution system distributes the reports to recipients. More specific steps regarding the distribution of the reports are presented in connection with FIG. 13.

Preferably, the method steps corresponding to the receipt of data stream module 110 and report reader module 140 are accomplished for each source input interface using multi-tasking programming techniques as is well known to those skilled in the art. Further in the preferred embodiment, the method steps corresponding to the report distribution module 180 are accomplished for all processes of the information distribution system.

Figure 6:
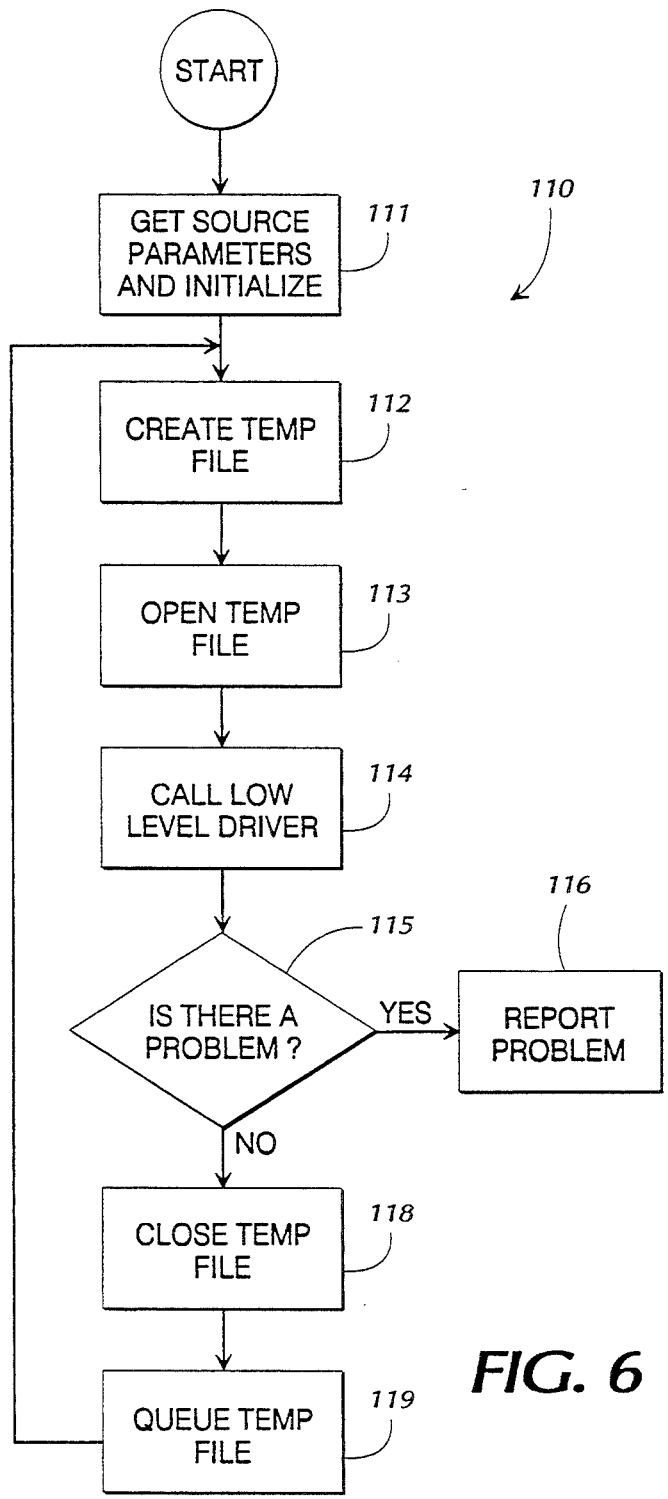

The flow chart in FIG. 6 illustrates the steps of the preferred embodiment of the present invention corresponding to receipt of data stream module 110 shown in FIG. 5. In order to service one or more reports from a source, at step 111 the system obtains parameters corresponding to the source and initializes the communication interface pursuant to the predetermined peripheral device protocol in the known manner. In the preferred embodiment, these parameters are obtained from a database (maintained in the databases 16) which has been set up with entries of the parameters of the serviced sources. Typical source parameters that are required include the identity of the printer protocol that is expected from the source's equipment, the identity of any network communication protocols that may be expected from a network interface, and positional information as to the location of the first ASCII character within a string of ASCII characters of a report.

Generally, the source parameter database in the system is set up at the time of installation. However, the source parameter database should be updated on a routine basis with the addition of new sources or with changes in the source parameters.

After initialization at step 111, the system is ready to receive a report. At step 112 in FIG. 6, the system creates a temporary file by assigning a temporary file name in accordance with operating system conventions, and at step 113 opens the temporary file in anticipation of the receipt of a digital data stream from a source. At step 114, a low level or device driver is called in order to establish communication with the source. More specific steps regarding the low level or device driver are presented in connection with FIG. 7.

At step 115 in FIG. 6, the system checks for a problem in the receipt of the data stream, such as whether a print file has only been partially received, whether communications with the source have been disrupted, or whether the queue of temporary files is full so that a "wait" condition exists for the queue to clear out. If the check in step 115 reveals there is a problem in the receipt of the data stream, the problem is reported in step 116 and handled by separate means.

If the check in step 115 is negative, the program flow passes to step 118. It will be understood that the end of a report or set of reports is detected by the time-out step described in connection with FIG. 7. Thus, when the timer described in FIG. 7 expires and characters have been received, it is deemed that the end of a report or set of reports has occurred and the temporary file is closed and passed to the queue for further processing. Steps are then taken to treat each set of characters as a page in a report or as a separate report. (See FIG. 10 and the discussion concerning the identification or delimiting of individual reports.)

The temporary file is then closed in step 118. In step 119, the system queues the temporary file for processing as described in connection with report reader module 140. Thereafter, the system is ready to repeat the steps associated with the receipt of data stream module beginning with the creation of a temporary file in step 112.

It will be understood at this juncture that the steps of receiving report files, shown in FIG. 6, occur repeatedly and asynchronously, so that reports are received and stored in memory in a first-in first-out (FIFO) queue for subsequent processing. It will also be understood that the method of allocating memory space, calling drivers, assigning temporary file names, queuing files for subsequent processing by passing file names to other processes, etc. is conveniently handled using procedure calls provided in the controller's operating system software.

Figure 7:
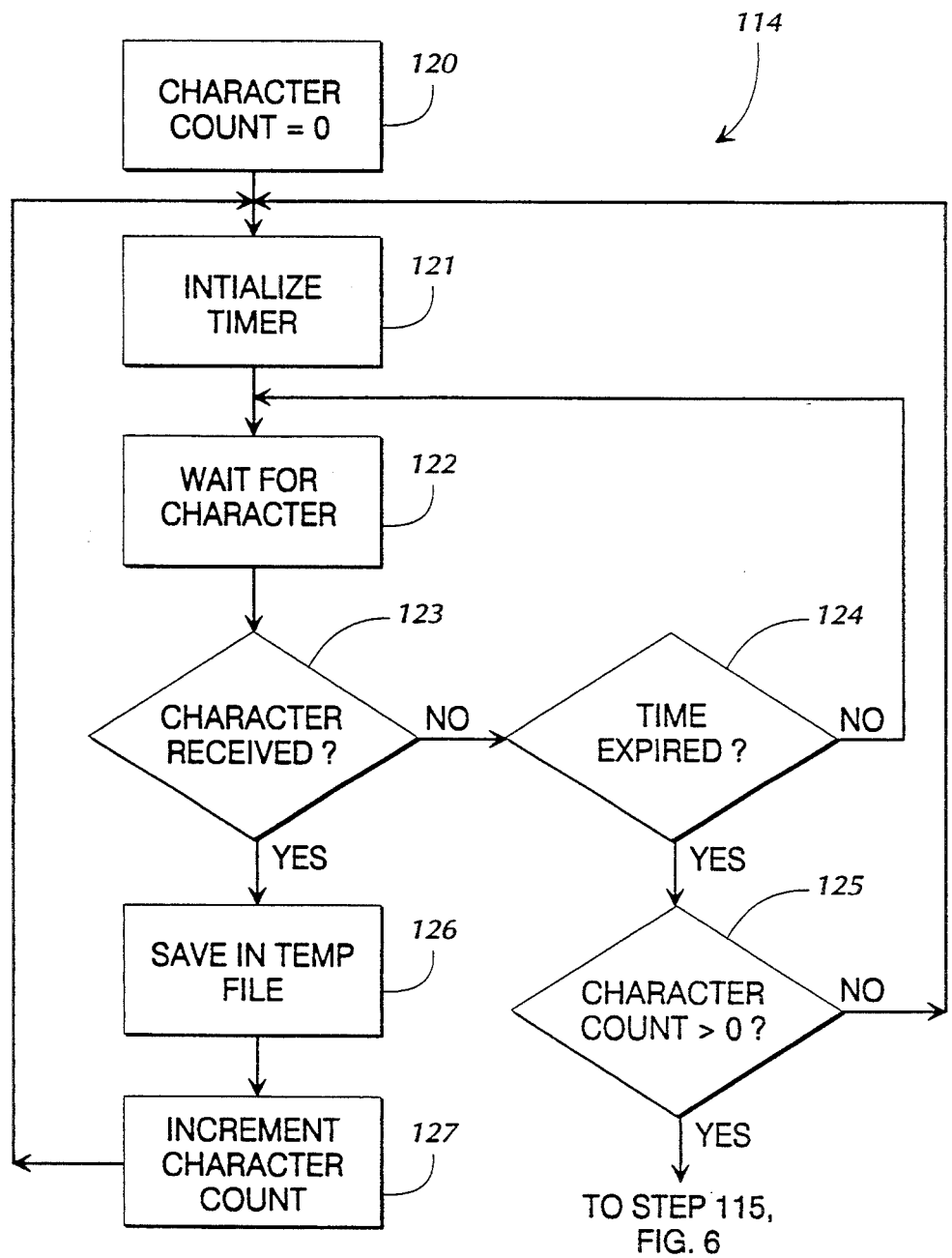

FIG. 7 illustrates the steps relating to the step of calling the low level driver 114 of FIG. 6. As an initial step, at 120 a character count is set equal to zero, and in step 121, a timer is set according to a predetermined parameter corresponding to a maximum desired time-out period within which the next character must be received lest the report be deemed complete. In the preferred embodiment, the timer is set to fifteen seconds. Step 122 comprises waiting for the characters comprising the data stream. In step 123, a check is made to determine whether a character has been received, generally by polling an associated serial interface. If a character has not been received, a check is made in step 124 to determine whether the timer of step 121 has expired since the wait for the characters began. If timer has not expired, steps 122 and 123 are repeated in that waiting for the characters continues followed by a check to see whether a character has been received.

If the check in step 124 indicates time has expired, a check is made at step 125 to determine whether the received character count is greater than zero. If the received character count is zero, the system returns to step 121 of setting the timer in accordance with the source parameter. If, on the other hand, the check in step 125 reveals that the character count is greater than zero, the system proceeds with checking for problems, etc. as described above in connection with FIG. 6.

Still regarding step 123, if the check for characters received is positive, the character(s) are saved in the temporary file pursuant to step 126. In step 127, the character count is incremented to indicate the receipt of a character, and the system returns to step 121 of setting the timer in preparation for the receipt of the next character.

Those skilled in the art will understand that the low level driver 114 of FIG. 7 is carried out for each character received by the system, until the steps of FIG. 6 indicate that the timer has expired and at least one character has been received, so that the temporary file should be closed. It will also be understood that other methods for receiving a report file such as by direct memory access (DMA), print file spooling, optical character recognition (OCR) of a preprinted report, and the like are considered equivalent methods to the steps of FIGS. 6 and 7 since all involve the provision of a report containing predetermined destination identifying indicia, report classification and/or subclassification indicia, and or other report identifying indicia in a manner that can be operated upon utilizing the preferred embodiment of the present invention, to distribute the report in an automated, rapid manner. It will thus be understood that the important aspect of FIGS. 6 and 7 are that these method steps, carried out by the controller 14, comprise means and a method for receiving a report for distribution by the system.

The flow chart of FIG. 8 illustrates the steps of the preferred embodiment of the present invention corresponding to report reader module 140 of FIG. 5. At step 141, the parameters corresponding to the source are obtained and the interface is initialized. Selected (and generally unnecessary) printer and/or communication control codes are removed, if necessary, from the queue file in step 143. More specific steps regarding the removal of control codes are presented in connection with FIG. 9.

Generally, a digital data stream corresponding to a report includes various control codes for formatting the digital data stream including codes for carriage return, line feed, page length and margins, etc. The control codes may also include address codes or signals relating to the addressing of the report via a network to a peripheral device such as a printer. In the preferred embodiment, the system removes any superfluous control codes relating to the direct printing and internal system handling of the document. Thus, if a digital data stream corresponding to a lab report prepared by a hospital laboratory includes control codes directing the report via the hospital's data communications network to the lab's printer, such control codes are removed to prevent printing of the lab report at the lab's printer. Alternatively, the printer codes may be ignored by designating a memory pointer to point to the beginning location of actual ASCII characters of the report, subsequent to any preceding or initial printer codes.

Optionally, the lab report may be printed at the lab's printer as well as provided through the system to the report recipient. Other control codes may be removed depending upon the preference of the user of the system. In applications such as shown in FIG. 3A, the primer codes would be preserved for reports that are to be passed through to the printer 17, while in the applications of FIGS. 3B and 3C, there is no need to preserve any printer codes so the codes are stripped.

As further illustrated in FIG. 8, after the control codes are removed in step 143, the data stream is analyzed in step 144. Generally, the system reads or scans the data stream for selected data fields corresponding to information used in distributing the report to recipients. It should be noted that in the preferred embodiment of the present invention, all of the selected data fields of a particular report are read at one time. The scan is based upon predetermined positional and reference cues or flags indicating the selected data fields in the report. The use of a positional cue, a reference cue, or both to indicate and identify a selected data field depends upon the user's data processing system including the predetermined peripheral device protocols and the set-up or format of the particular report. The use of such cues or flags is set up at the time of installation of the system with a particular source, and is updated as necessary. More specific steps regarding the analysis of the data stream are presented in connection with FIG. 10.

In particular, however, it will be understood that a report such as the report 20 in FIG. 4 will contain identifying information at predetermined positional locations in a report, depending upon the report format. By way of example but not of limitation, and assuming a rather conventional 80-column print format, a hospital ID field or indicia 38 may appear on line 1, beginning at the fifth character; a patient number field or indicia 21 may appear on line 5, beginning at the fifth character and extending for a maximum of forty characters; an ordering physician name field or indicia 28 may appear on line 5, beginning at the fiftieth character position and extending to the end of the line; a report type or classification field or indicia 23 may appear on the tenth through fifteenth line, somewhere on the line, etc. Such examples are considered "positional cues" since the fields or indicia are located at certain predetermined positions on a report page.

Continuing with the example, "reference cues" are similar but instead of being at a predetermined position, contain predetermined identifying information. Most report formats generated by hospitals and other institutions will be substantially "form-like" in that the final printed appearance of the report will be that of a preprinted form, containing boxes, border and divider lines, and identifying headers. An identifying header such as HOSPITAL ID, or PATIENT NO., or LAB REPORT, or ORDERING PHYSICIAN, will often form a regular part of a given report. If such identifying indicia are used in the report's format, such information will be embedded in the print file as ASCII characters, and may therefore serve as a reference cue that the information following the header, within a predetermined range of positions, will be of the type specified. Thus, it can be expected that a patient number identifying field or indicia will follow a header identified as such.

Likewise, relative positional cues will be used together with reference cues to locate the appropriate identifying indicia. In the example just discussed, a relative positional cue comprises an indication that the indicated field or indicia is located within a predetermined range of character counts and/or lines from the reference cue. In such a case, desired identifying information is located both by an indication of a header flagging its imminent appear and a position relative to the header.

Inasmuch as there will be many different formats and structures of reports, appropriate positional and reference cues will generally be needed as elements of the source parameters of step 111 of FIG. 6. It will thus be appreciated that the step 144 of FIG. 8, involving an analysis of the data stream, comprises a character and/or word scan of a received print file, looking for report identifying indicia based upon selected positional and/or reference cues.

Still referring to FIG. 8, in step 145 the system optionally augments the report contained in the queue file with predetermined header information. Specifically, as shown in the generalized report of FIG. 4, certain identifying information 37 may be prepended to the report. This identifying information 37 may include, inter alia, identification of the hospital 38 or other source which generated the report. It will be understood that in some cases the print file received from the source 15 may not include all appropriate header information that may be desired by report recipients, and such additional information may be added to a distributed report with the present invention in the form of a header or overlay. For example, it will be understood that many reports are intended to be printed in a graphic form, with logos, borders, and perhaps other graphic information. Such graphics may be provided on the stationery used by the report generating source when it prints using its printer. In other cases, such graphic information is often provided in POSTSCRIPT ®, TRUETYPE ™, or other similar graphic page description languages. Therefore, the present invention is optionally operative in step 145 to augment or overlay the report with any desired appropriate additional information.

The header information may also contain patient name, date, report type or other identifying information. In many cases, header information appears at the top or beginning of a report as distributed to the recipient, thereby specifically identifying the report to the recipient. In this use, the header information takes the place of preprinted information, letterhead, or particularized forms used by the source as the general report stationery. Also, the header information is used preferably to facilitate the archival of reports by the hospital or other source. Additional steps regarding the augmenting of the report are discussed in connection with FIG. 11.

After the report is augmented in step 145, in step 146 the selected data fields resulting from the analysis of the data stream in step 144 are compared to database entries corresponding to the subject matter of the selected data field. The method of comparing selected data fields to a database, for example by utilizing the identification information as an index or pointer to database entries, is well known to those skilled in the art. Nonetheless, for the sake of clarity steps of the present invention comprising the comparison of step 146 are presented in FIG. 12. As a specific example, as shown in FIG. 1 in connection with the preferred embodiment of the present invention, data field 28 corresponding to the identity of the ordering physician, "Smythe", is compared with physician name entries 41 in database 16a for a matching entry.

Referring again to FIG. 8, in step 147 a check is made for a matching database entry corresponding to the selected data field. If a matching entry is not found, and assuming that the principal identifying information being examined is ordering physician, it is assumed that the physician's name appearing in the report is not contained in the database 16a and preferably the contents of the queue file are sent in step 148 to a printer associated with the source. However, the unmatched queue file may be held pending a match-up provided by the source, or otherwise distributed pursuant to user preference. Thus, in the example of the hospital lab report, if a matching database entry is not found for the selected data field 28 of FIG. 1 corresponding to the identity of the ordering physician, Dr. Smythe, or in other words, if the database has no cross-reference for the Dr. Smythe, the preferred embodiment of the present invention prints the report at the hospital laboratory's printer.

According to another aspect of the invention, the system 10 provides for automatically updating the database with information relating to the unmatched selected data field. Steps for updating the database are presented in connection with the example of the hospital lab report in FIG. 12.

Figure 12:
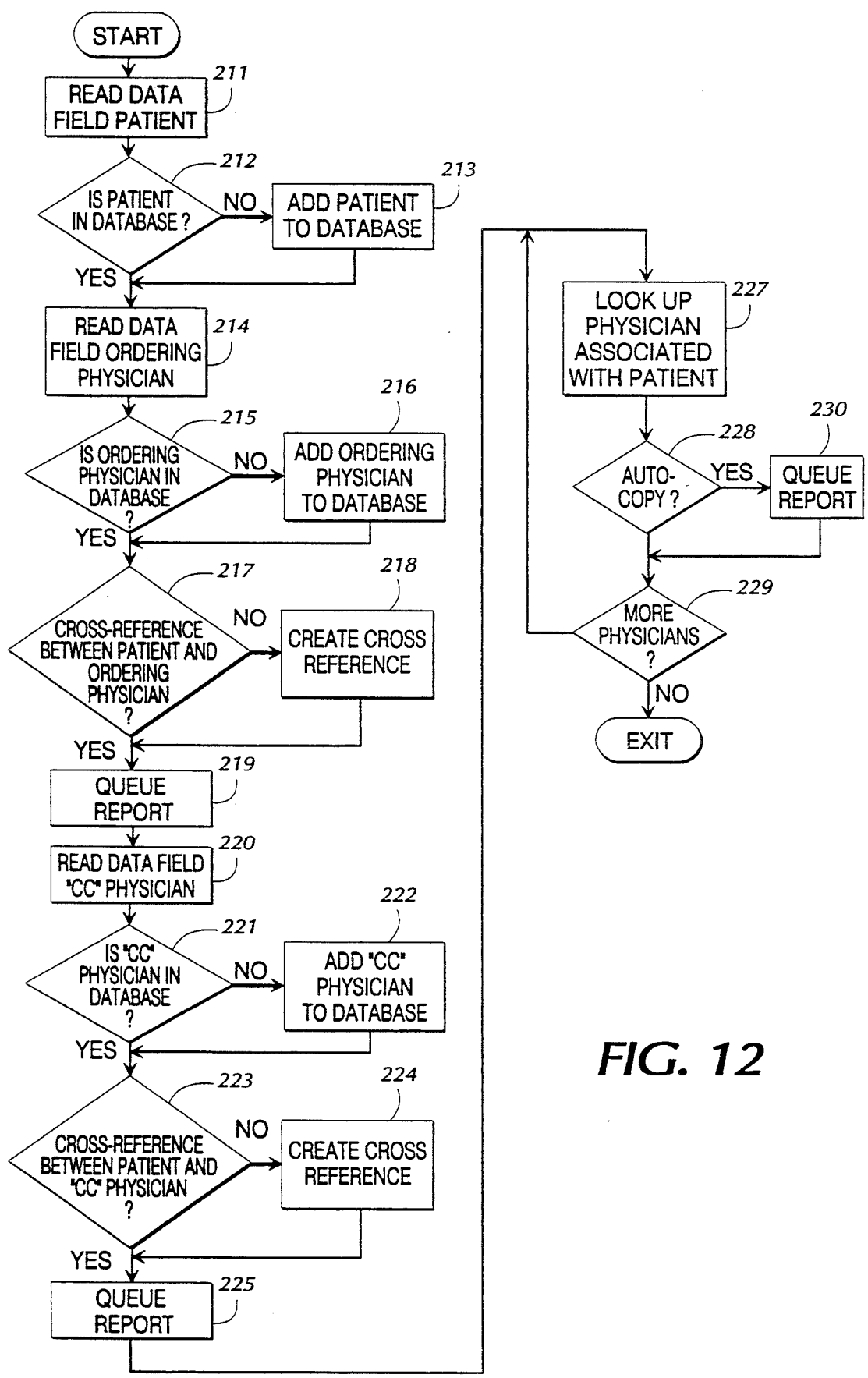

If, on the other hand, a matching entry is found for the selected data field, the queue file is saved in step 149 as part of a final update function before the report contained therein is distributed to report recipients. More specific steps are illustrated in FIG. 12 regarding the updating of the database as presented in connection with the hospital lab report example shown in FIG. 4. After update step 149, the system proceeds to distribution of the report, which comprises more specific steps presented in connection with FIG. 13.

The flow chart of FIG. 9 illustrates specific steps regarding the step of removing control codes 143 of FIG. 8 in the preferred embodiment. In particular, at step 151 the system reads the contents of a queued temporary file. As noted above in connection with step 119 in FIG. 6, the received digital data stream is saved in a temporary file and queued, by passing the file name of the queued temporary file to the report reader module. Step 152 checks whether the contents of the queued file are to be printed, and step 153 sends the queued file to the printer if the response to the check in step 152 is affirmative.

It should be understood that the step of printing the queued file is optional in the preferred embodiment of the present invention. For example, in the configuration of FIG. 3A, the system 10 effectively intercepts a print file; the intercepted file may be distributed by the system 10, may be forwarded "as is" (that is, without stripping the printer codes) to a connected printer for printing, or may be both distributed and printed locally. Thus, a user is offered the option of printing the report at a selected printer such as the printer at the location where the report is generated, i.e., at the hospital laboratory location.

After the queued file is sent to the printer in step 153, or after receipt of a negative response with respect to a check in step 152 of whether to print the queued file, the system carries out two additional optional steps. In step 154, print codes which are not emulated by the system (that is, unnecessary for identifying and distributing the report to an intended recipient) are removed from the digital data stream, for example, a fax modem used to distribute the report may not need certain font and size commands in order to generate the facsimile file. Similarly, in optional step 155, non-emulated escape codes are removed. The system may provide for emulation of POSTSCRIPT ®, HP (conventional Hewlett-Packard printer protocol), or TTY codes. As noted previously, the report may be printed pursuant to the print or escape codes as well as distributed to report recipients in accord with the steps of the present invention.

It should be understood that the received digital data stream may contain more than one report, comprising a plurality of reports in a particular class of reports, or comprising a plurality of reports in different classes of reports. Preferably, each report handled and analyzed in step 144 may be identified as being of a member of one or more classes or subclasses or reports, where each class or subclass identifies particular characteristics of the report, for example, lab reports, cardiology reports, cardiology reports for inpatients and for outpatients, etc. According to another aspect of the invention, information corresponding to the class and/or subclass of each report analyzed is stored in a class file, enabling the report generators or report recipients to retrieve the class file at a later time as a historical record, or to use the class information for statistical or research purposes.

FIG. 10 illustrates steps comprising step 144 shown in FIG. 8 of analyzing the data stream. As described above, the received digital data stream 30 may contain more than one report, or a report may contain more than one page, before the end of the temporary file is encountered. The system begins its analysis in step 158 by reading the temporary file created in FIG. 6, a line at a time (it being understood that a "line" is typically delimited by a carriage return and/or line feed character). At step 159, each line is scanned to detect the presence of a predetermined primary class identifier. If at step 159 a primary class identifier is found on the line being examined, the YES branch is taken to step 161 where the inquiry is made whether a secondary class identifier (if any for the particular primary class identifier) is present, in a predetermined position relative to the primary class identifier.

It should be understood at this juncture that a report or class of reports may be identified by a single class identifier, or by a primary class identifier together with one or more secondary class identifiers. For example, and referring to FIG. 4, a report of the type or class "LAB REPORT" might be identified by the primary class identifier comprising the characters LAB REPORT occurring on the fourth line of a report. The presence of these characters on any line, however, would likely indicate that the temporary file being analyzed is a laboratory report of one type or another, but in order to be certain, additional information (the secondary class identifier) would be sought so that the extraneous presence of the character string "lab report" does not causes the treatment of the particular temporary file as a lab report.

The classification of the report as a LAB REPORT, however, might require the further or secondary class identifier located at a predetermined position relative to the primary class identifier LAB REPORT. For example, in the report of FIG. 6, a secondary class identifier might be the character string HOSP. ID (for hospital identification) located three lines before the primary class identifier. The presence of one or more secondary class identifiers at one or more predetermined locations relative to a primary class identifier then uniquely identifies the particular section of temporary file being examined as being in a particular class of reports. Thus, at step 161 the data contained in the temporary file is identified as being a member of a particular class of reports, if the appropriate secondary class identifiers are present.

Returning now to step 159, if no primary class identifier is found on the line being examined, the NO branch is taken to step 160, where the inquiry is made whether all lines in the temporary file have been examined. If not, the program loops back to step 158 and the next line is examined for the presence of primary class identifiers.

If at step 160 all lines of the temporary file have been examined without encountering any primary class identifiers, the entire temporary file is handled at step 163 as "unknown", by steps not illustrated.

Similarly, at step 161, if no appropriate secondary class identifier has been found such that the report can be properly classified (i.e., the requisite primary and secondary class identifiers have not been found, the program takes the NO branch and loops back to step 160 to continue to examine the next line of the temporary file.

If the requisite secondary class identifier for the particular primary class is found at step 161 is found, the YES branch is taken the step 162. At this step, the inquiry is made whether the start of the report that has now been deemed to be a member of a particular class (e.g., the report has now been classified as a LAB REPORT) is coincident with the current position in the temporary file. It will be appreciated that a given temporary file may contain more than one report. The preferred software utilizes pointers to positions in the temporary file indicative of the current position within the temporary file. Once a given report has been identified and located, it may be processed as a report and passed to the queue for distribution, and the pointer advanced to the next report.

Under many conditions, the start of a report will (and should) coincide with the current position in the temporary file. However, it should be understood that for various reasons, the temporary file being processed may include unknown data, or data forming a part of an earlier report. In such cases, the requisite primary class identifier might not be located at a particular position relative to the beginning of the temporary file. For example, it is possible that the primary class identifier might occur virtually anywhere in the temporary file, for example when the temporary file contains unknown material together with an identifiable report.

Continuing the example of FIG. 4, assume that the primary identifier LAB REPORT appears on the 50th line, and that a secondary class identifier HOSP. ID appears in its proper predetermined location three lines before LAB REPORT. In such a case, the prestored classification information would indicate that a "lab report" of the class being identified begins four lines before the character string LAB REPORT as a primary class identifier, such that the 46 lines preceding the calculated beginning of the report are unknown and are not a part of the report being handled.

Accordingly, if at step 162 the start of the report of the identified class of reports is not coincident with the current position in the temporary file, the NO branch is taken to step 164, where the data not forming a part of the report (e.g. the preceding 46 lines of the example given above) is classified as "unknown" and handled as such by other program steps (not illustrated).

If the start of the report of the identified class of reports is coincident with the start of the temporary file, the YES branch is taken to step 165.

Also as noted above, each report is classified by the system into classes and subclasses, depending upon the information contained in the report. In order to accomplish such classification and subclassification, the system is provided at the time of its set up or initialization with information to be used in classifying and subclassifying the reports transmitted by the serviced source. This information includes positional flags or reference flags keyed to each class and subclass of reports. The information is stored in the database 16 by the system as initial parameters, and is called upon in classifying and subclassifying reports.

As noted above, the system scans for class identifying information by searching for positional flags or reference flags as described herein. Thus, the system classifies report 20 of FIG. 4 as being in the lab report class. As many different classes of reports may be provided as necessary. Typically, each report source 15a, 15b, ... 15n will be in a different class, facilitating differentiation of reports by source. Hospital face sheets, which are typically generated by an ADT (admission, discharge, transfer) system, will generally constitute a separate class, and additional subclass identifying information is generally needed for further classification purposes.

After step 162, the system proceeds to step 165 wherein a check is made as to whether the system should "drop" the report. Dropping a report is equivalent to ignoring the report as if it were never transmitted to the system. In such cases, the report would not be distributed to intended recipients via the system 10, but typically would be passed through to the printer, printed in the conventional manner, and distributed manually. For example, certain sensitive reports such as HIV-positive blood test results may be dropped routinely on the basis of patient confidentiality. Thus, the preferred embodiment is operative to selectively drop or ignore a given report being processed based on the detection of predetermined drop indicia, such as the presence of sensitive subject matter or a particular flag such as "DO NOT FAX" embedded in the print file, with optional additional positional cues.

After a report is dropped, the system returns to step 158. If the report is not dropped, a check is made in step 166 as to whether the class of the report is broken into subclasses, that is, whether the report also contains predetermined subclass identifying information. If the class has subclasses, in step 167 the report is read for data fields indicating a subclass. For example, report 20 of FIG. 4 is classified as a lab report based on data field 23, and subclassified as an in-patient report based on data field 26. An in-patient subclass lab report may be designated for distribution by the system 10 to a local hospital ward's fax machine, while an out-patient subclass lab report may be designated for distribution to a referring physician's fax machine via the system. Thus, it will be appreciated that the provision of subclasses for a given class of report allows the system to handle and distribute different subclasses of the report differently, if needed.

If there are no subclasses in the class, or after the report is read for subclasses in step 167, the report is read for information indicating the end of the report in step 168. Such an indication may be a preselected protocol sequence or code, escape code, EOF indicator, or other preselected information provided in a data field of the data stream. In the preferred embodiment, the end of a report is typically indicated by a predetermined number of lines on a page (typically 66) or a standard form feed character. If the system is unable to determine the end of a particular report, its preferred default mode is to treat each page (the end of which is typically identified by a form feed command or code) as a separate report, thereby assuring that the recipient obtains a complete copy of the report.

It should be understood that the preferred handling of classes and subclasses is as follows—a given report is first analyzed as to whether the report is classified within a given class, e.g. lab report. Reports identified as being members of a particular class are handled normally, that is, sent to ordering physicians in the described manner. However, the presence of subclass identifying indicia, such as the inpatient indicia or field 26 in the exemplary report in FIG. 4, may cause the normal handling to be overridden. Thus, if a lab report for a hospital inpatient should be sent to a local ward or nurse's station fax machine, the destination information can be overridden with the destination override field in the class table 16e in FIG. 1. Otherwise, if the inpatient indicia 26 shows the status of a patient as being outpatient, the report can be sent to the ordering physician as the indicated destination in the normal manner.

As another example of the handling of particular reports as to class, it will be understood that hospital face sheets include important administrative information that many, if not all, associated physicians will want to receive, such as social security number, address, known allergies to drugs, prior medical history, etc. Thus, reports classified in the "face sheet" class may be targeted for special handling or to be sent to special destinations. In particular, face sheet reports may be flagged, via the class table 16e, for transmission to all physicians associated with the identified patient in the patient name table 16d (thus making relational databases preferred for use in the present invention).

The addition of a new physician to the database leads to similar special treatment of predetermined report classes. It may be desirable in some applications of the present invention to have all reports of a certain class, e.g. face sheets for a particular patient that have been generated earlier but are still readily available on hard disk or retrievable archive, to be automatically retrieved from storage and transmitted to a newly added physicians. To implement this feature, all that is required is to modify the steps of FIG. 13 pertaining to updates of the physician databases to include steps of retrieving predetermined classes of previously generated reports and for transmitting such reports to the newly added physician. In this manner, a new physician who is associated with a patient can be made to automatically receive one or more prior reports of a historical or administrative nature, to facilitate his or her getting familiar with the case and handling the usual administrative paperwork.

Figure 11:
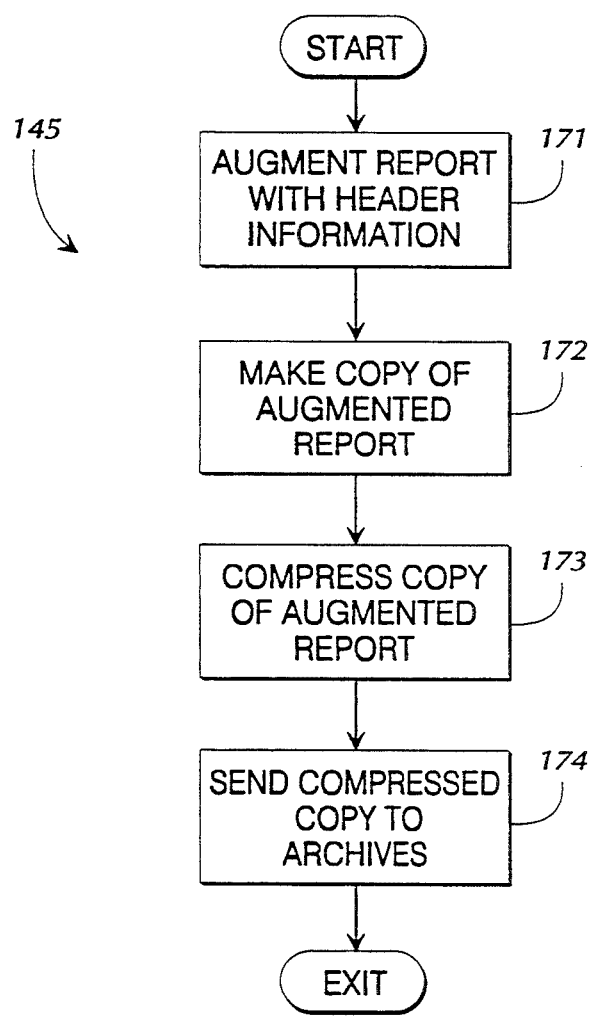

FIG. 11 illustrates the steps of the preferred embodiment of the present invention comprising step 145 of FIG. 8 relating to augmenting and archiving the report. In particular, in step 171 the report is augmented with header information such as discussed in connection with FIG. 4. In step 172, a copy is made of the augmented report by duplicating the file in memory, and in step 173 the augmented report is compressed using methods of data compression well known to those skilled in the art. In step 174, the compressed augmented report is sent to archives for later use or retrieval, as desired by the recipient or the source. In particular, it will be understood that one or more of the output ports 18 may be connected to a data storage device such as an optical disk drive, tape drive, or the like, for archival storage purposes. After archival, the system exits and returns to step 146 in comparing data fields in the report to entries in at least one database, as discussed above in connection with FIG. 8.

The flow chart of FIG. 12 illustrates the steps of the preferred embodiment corresponding to comparison step 146 and matching entry check step 147 of FIG. 8. FIG. 12 also illustrates steps for updating databases as applied in the preferred embodiment of the present invention. Generally, as explained above, the system scans the digital data stream for selected data fields corresponding to information regarding the recipient of the report, by reference to positional and/or reference cues. In the particular example given, such selected data fields comprise references to a patient, an ordering physician, a "cc" physician, or an auto-physician. In FIGS. 3 and 4, references to the patient are in data field 27, the ordering physician in data field 28 and to the "cc" physician in data field 22.

In particular, in step 211 the data field 21 of a report corresponding to the identity of the patient is read. In step 212, a check is made to determine whether there is a matching entry in the patient name table or database 16d corresponding to the identity of the patient. If there is no matching entry, the patient is added to the database 16d in step 213 and the system proceeds to step 214. If a matching entry for the patient is found, the system proceeds directly to step 214.

In step 214, the data field 28 corresponding to the identity of the ordering physician is read. A check is made in step 215 to determine whether the ordering physician is in the database 16a, 16b, and 16c. If not, the ordering physician is added to the database(s) in step 216, where appropriate, and the system proceeds to step 217. For example, a variant spelling of a particular physician may appear for the first time in a report, but other correlating indicia contained in the physician master table, physician profile table, or patient name table may allow an automated determination that this new spelling is a variant of an existing physician entry, and an new entry is added the the physician name table 16a. Alternatively, a physician may be added to the system with the use of a special class of reports (e.g. an update report) specifically for the purpose of adding names, addresses, fax numbers, etc. to the databases.

If the ordering physician is already in the database, the system proceeds directly to step 217. A check is made in step 217 to determine whether a cross-reference exists in the database 16d between the ordering physician and the patient. If a cross-reference does not exist, it is created in step 218. After creation of the cross-reference in step 218, or after the check of step 217 for such a cross-reference is found to be positive, the system queues the report for distribution to recipients in step 219. Additional steps regarding the report queue are presented in connection with FIG. 13.

The system follows similar steps in reading and comparing the identity of one or more "cc" physicians and auto-physicians for matching entries in the databases 16b, 16c in order to obtain destination information. In step 220, the system reads the data field corresponding to the identity of at least one "cc" physician. A check is made in step 221 to determine whether there is a matching entry for a "cc" physician in the database. If not, the "cc" physician is added to the physician profile table 16c as a "cc" recipient in step 222. After adding the "cc" physician to the database, or after a positive response to the check of step 221 for the "cc" physician in the database, a check is made in step 223 to determine whether there is a cross-reference between the patient and the "cc" physician. If there is no cross-reference, it is created in the patient name table 16d in step 224.

After creation of the cross-reference or after the check of step 223 for the cross-reference is found to be positive, the system queues the report in step 225 and proceeds to step 227. It will be understood that the steps are repeated for as many "cc" physicians as required.

In step 227, the system looks up the identification and destination information information for any physicians associated with the particular patient identified in the report. It will be recalled that, typically, a particular patient on the report is identified in step 211; preferably, the patient ID is used to index into the database to determine whether there is a physician associated with this particular patient that has indicated a desire to receive an autocopy. If at step 228 the associated physician is to receive an autocopy, the report is queued to be sent to the autocopy physician at step 230, and the program proceeds to step 229.

At step 229, if the inquiry in step 228 for the particular associated physician is a NO on autocopy, or after queuing the report to such associated physician at step 230, the inquiry is made whether there are any more physicians associated with the particular patient. If not, the routine comprising of FIG. 12 exits. If so, however, the program loops back to step 227 to find any more associated physicians for autocopy purposes.

After the report is queued, the destination of the analyzed report has now been identified, primarily by identification of appropriate recipients. The program of FIG. 12 is complete, and further steps are taken to distribute the report. It will be noted that the various steps 219, 225, and 230 for queuing the reports to ordering physician, "cc" physician, and auto physician, ensure that each different category of report recipient receives the report. It will thus be understood that the program could be altered to provide for the transmission of a single queued report to a plurality of recipients (which conserves memory space), or the single report can be queued multiple times for each individual recipient.

Figure 13:
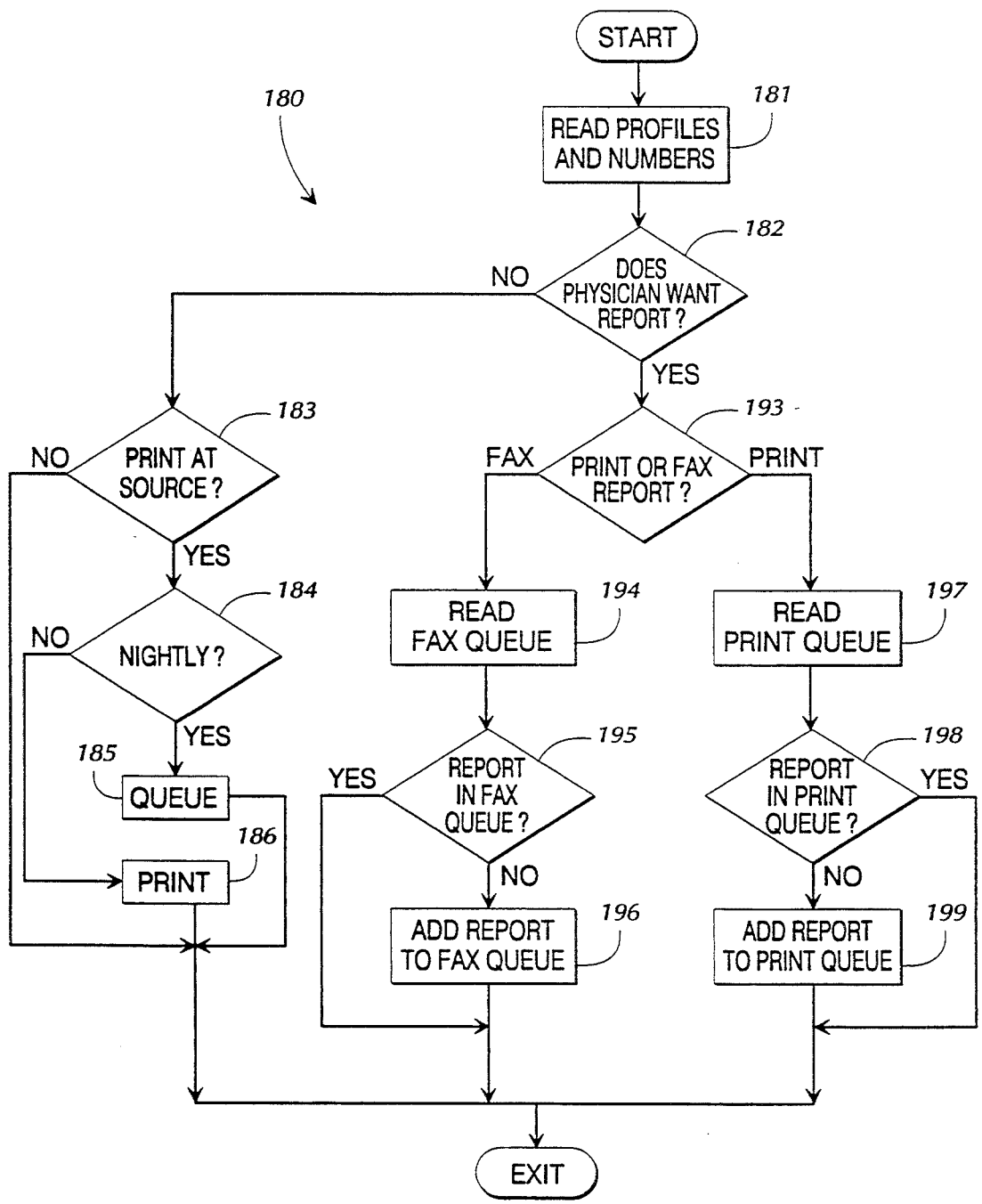

FIG. 13 illustrates the steps of the preferred embodiment of the present invention relating to distribution of the report, assuming that reports have been queued as described the report recipients identified by the module 140, and identification information as to the report recipients (for example, the fax number(s) of all report recipients) passed as parameters to the module 180. The steps of FIG. 13 comprise steps forming the report distribution module 180 of FIG. 5. Starting at step 181 of FIG. 13, the system reads the destination information passed as destination parameters. In step 182, a check is made to determine whether the physician wants a copy of the report. This is primarily conducted by examining the physician profile table 16c to see whether the recipient has indicated that he or she wants the copy.

If not, a check is made in step 183 to determine whether the report should be printed at the source. If the report is not to be printed at the source, the system turns its attention to the next report. If the report is to be printed at the source, a check is made in step 184 to determine whether the report should be printed together with other reports after office hours, typically at night. If the report is not to be printed after office hours, the report is sent to the printer in step 186. If the report is to be printed after hours, the report is queued for such later printing.

Referring again to step 182 of FIG. 13, if the physician desires a copy of the report, a check is made in step 193 to determine whether the report is to be distributed by fax or by primer. If the report is to be faxed, the fax queue is read in step 194. Then, in step 195, a check is made of whether the report is in the fax queue. Once the report is in the fax queue, it will automatically be transmitted by the fax modem internal to the system 10 for transmission to the report recipient. If the report is not in the fax queue, the report is added to the fax queue in step 194.

Similarly, if the check in step 193 reveals that the report is to be printed, the print queue is read in step 197. A check is made in step 198 to determine whether the report is in the print queue. If not, the report is added to the print queue in step 199, and the report will be printed in due course.

It will of course be understood that the queuing of reports for printing and/or faxing comprises steps within the capabilities of a person skilled in the programming arts, mainly be establishing a circular FIFO buffer containing the report files that have been stripped as described herein, with a queue handler being responsible for receiving data indication of the location of the beginning and end of a report file, and appropriate destination information such as fax number of a recipient.

It will also be understood that the software utilized in the disclosed embodiment, once passed the starting location of a file to be sent by facsimile and a fax number, is then automatically operative to transmit the file by facsimile using the fax board, and to signal the queue handler when the fax board is idle and ready to transmit another file. For example, Intel Corporation brand fax boards, which are suitable for use in the present invention, support the Intel Communicating Application Specification (CAS) that is a software interface supported by Intel fax boards. Many other types of fax boards, also suitable for use in the present invention, can be controlled directly via a special set of AT commands, known to those skilled in the art, as specified in the Electronics Industries Association (EIA) Class 1 and Class 2 Asynchronous Facsimile Control Standards (EIA/TIA-578).

In similar fashion, if the fax board software encounters difficulties with or interruptions in the transmission, it typically will pass error parameters to the queue handler. The queue handler then is responsible for either re-queuing all or a part of a report for re-transmission, or for generating an error message to the system operator under predetermined conditions. Such error handling routines and procedures are considered within the skill of the art and will not be discussed further herein, except to say that the preferred embodiment employs such error handling routines in a conventional manner.

The preferred embodiment of the present invention has been disclosed by way of example and it will be understood that other modifications may occur to those skilled in the art without departing from the scope and the spirit of the appended claims.

What is claimed is:

1. In a data processing system including at least one report source operative to provide a report in the form of a data stream formatted according to a predetermined peripheral device protocol, a method for distributing the report to a report recipient, comprising the steps of:
   (a) receiving the report from the report source;
   (b) reading a selected data field from the report;
   (c) comparing the selected data field with at least one entry in a database to find a matching database entry corresponding to the selected data field;
   (d) in response to finding the matching database entry, identifying from the matching database entry at least one selected report recipient and destination information for the report associated with the selected report recipient; and
   (e) in response to identifying the selected report recipient and destination information, distributing the report to a destination corresponding to the destination information.

2. The method of claim 1, further comprising the step of, in response to a failure to find a matching database entry, providing the report to a selectable peripheral device associated with the report source.

3. The method of claim 1, further comprising the step of, in response to a failure to find a matching database entry, updating the database with information derived from the report.

4. The method of claim 1, wherein the step of reading a selected data field comprises the steps of:
   identifying a predetermined reference cue comprising at least one predetermined character; and
   utilizing the predetermined reference cue to locate the selected data field.

5. The method of claim 4, wherein the selected data field comprises a primary class identifier, and further comprising the steps of:
   identifying a predetermined second reference cue comprising at least one predetermined character, relative to the first reference cue;
   utilizing the predetermined second reference cue to locate a second selected data field; and
   utilizing the second selected data field as a secondary class identifier.

6. The method of claim 1, further comprising the step of utilizing at least one predetermined reference cue and at least one positional cue to locate the selected data field.

7. The method of claim 1, wherein the step of reading the selected data field comprises scanning the report for a positional cue indicating the selected data field.

8. The method of claim 1, wherein the step of reading a selected data field comprises:
   scanning the report for a reference cue; and
   scanning the report for a positional cue relative to the reference cue indicating the selected data field.

9. The method of claim 1, wherein the step of distributing the report to the destination comprises providing the report by facsimile transmission to the report recipient.

10. The method of claim 1, wherein the step of reading the selected data field comprises scanning the report for a reference cue indicating the selected data field.

11. The method of claim 10, wherein the reference cue comprises a predetermined string of characters corresponding to at least one identifying label contained in the report.

12. The method of claim 1, wherein the step of providing destination information further comprises the step of augmenting the report prior to distributing the report.

13. The method of claim 12, wherein the step of augmenting the report comprises adding predetermined information to the report prior to distributing the report.

14. The method of claim 1, further comprising the step of automatically storing the report in a data archive.

15. The method of claim 14, further comprising the step of data compressing the report prior to storing the report.

16. The method of claim 1, wherein the step of reading a selected data field comprises:
scanning the report for report class identifying indicia corresponding to at least one report class;
utilizing the report class identifying indicia to find a database entry corresponding to the report class; and
utilizing information contained in the database entry for the report class to control the distribution of the report.

17. The method of claim 16, wherein the step of utilizing information contained in the database entry for the report class to control the distribution of the report comprises directing the report to a location other than the location corresponding to the destination information, whereby the information in the database entry for the report class overrides the destination information.

18. The method of claim 16, wherein the step of utilizing information comprises withholding the distribution of a predetermined class of reports to a particular intended report recipient, whereby a report recipient can indicate that he or she does not wish to receive particular class or classes of reports.

19. The method of claim 16, further comprising the steps of:
scanning the report for report subclass identifying indicia corresponding to at least one report subclass;
utilizing the report subclass identifying indicia to find a database entry corresponding to the report subclass; and
utilizing information contained in the database entry for the report subclass to control the distribution of the report.

20. The method of claim 1, wherein the report includes control codes corresponding to a predetermined peripheral device protocol, and further comprising the step of selectively removing at least one of the control codes from the report.

21. The method of claim 20 wherein the control codes include printer format codes, and wherein the step of removing at least one of the control codes comprises removing at least one of the printer format codes.

22. The method of claim 20, wherein the control codes include escape codes, and wherein the step of removing at least one of the control codes comprises removing at least one of the escape codes.

23. The method of claim 1, wherein the step of receiving the report comprises:
establishing communication with the report source via a communication means;
in response to establishment of communication, creating a temporary file;
accepting the report from the report source through the communication means as a plurality of data items; and
in response to acceptance of the report, storing the report in the temporary file.

24. The method of claim 23, wherein the step of receiving the report comprises:
checking the data items in the temporary file for an instruction to send the report to a peripheral device associated with the report source; and
in response to finding the instruction to send the report to the peripheral device, transmitting the temporary file to the peripheral device.

25. The method of claim 24, wherein the peripheral device is a printer responsive to the predetermined peripheral device protocol for printing the report.

26. The method of claim 23, further comprising the steps of:
initializing a character count for the counting of characters in the data stream of the report; and
in response to receipt of a character, incrementing the character count.

27. The method of claim 26, further comprising the steps of:
initializing a timer with a selectable time period; and
in response to receipt of at least one character within the selectable time period, saving the character in the temporary file.

28. The method of claim 27, further comprising the steps of:
in response to the lack of receipt of a character within the selectable time period, checking whether the character count is zero: and
in response to a character count that is zero, re-initializing the timer with the selectable time period.

29. In a data processing system including at least one report source operative to provide a report in the form of a digital data stream having data fields corresponding to a predetermined peripheral device protocol, a method for distributing the report to a report recipient, comprising the steps of:
(a) receiving the report;
(b) reading a first selected data field from the report;
(c) comparing the first selected data field with at least one entry in a database to find a first matching database entry corresponding to the selected data field;
(d) in response to finding the first matching database entry, retrieving classification information for the report from the first matching database entry;
(e) reading a second selected data field from the report;
(f) comparing the second selected data field with at least one entry in the database to find a second matching database entry corresponding to the second selected data field;
(g) in response to finding the second matching database entry, identifying from the second matching database entry at least one selected report recipient and retrieving destination information for the report from the second matching database entry; and
(h) in response to the destination information, distributing the report to a destination corresponding to the destination information as modified by the classification information, whereby the report is distributed to the selected report recipient.

30. The method of claim 29, wherein the database includes entries corresponding to report recipient preferences, and wherein the classification information comprises indicia indicative that a particular report recipient does or does not wish to receive a particular class of reports.

31. The method of claim 29, wherein the destination information includes information corresponding to a primary destination to which a report is to be distributed, wherein the database includes entries corresponding to destination override, and wherein the classification information comprises indicia indicative that a particular report should be sent to a destination other than the primary destination in response to destination override.

32. In or for use with a system operative to provide a report in a digital data stream formatted according to a predetermined peripheral device protocol, apparatus for distributing the report to a report recipient, comprising:

an interface for receiving said report from a report source;

a database for storing destination information and report class information;

means for reading a first selected data field from said report;

means for comparing said first selected data field with at least one entry in said database to find a first matching database entry corresponding to said first selected data field;

means responsive to said first matching database entry for identifying from the first matching database entry at least one selected report recipient and retrieving said destination information for the report associated with said first matching database entry;

means for reading a second selected data field from said report;

means for comparing said second selected data field with at least one entry in said database to find a second matching database entry corresponding to said second selected data field;

means responsive to said second matching database entry for retrieving report class information for the report associated with said second matching database entry; and means responsive to said destination information and said report class information for distributing the report to the destination corresponding to said destination information as modified by said report class information.

33. The apparatus of claim 32, wherein the database includes entries corresponding to report recipient preferences, and wherein said report class information comprises indicia indicative that a particular report recipient does or does not wish to receive a particular class of reports.

34. The apparatus of claim 32, wherein said destination information includes information corresponding to a primary destination to which a report is to be distributed, wherein said database includes entries corresponding to destination override, and wherein said report class information comprises indicia indicative that a particular report should be sent to a destination other than the primary destination in response to said destination override.

* * * * *